(12) United States Patent
Serafin, Jr. et al.

(10) Patent No.: US 9,162,008 B2
(45) Date of Patent: Oct. 20, 2015

(54) CERAMIC MANUFACTURES

(75) Inventors: Louis A. Serafin, Jr., Lakeport, MI (US); Gerald J. Jerry, Jr., St. Clair, MI (US); Nicholas H. Burlingame, Belmont, NY (US)

(73) Assignees: Louis A. Serafin, Jr., Lakeport, MI (US); Xylon, L.L.C., Marysville, MI (US)

( * ) Notice: Subject to any disclaimer, the term of this patent is extended or adjusted under 35 U.S.C. 154(b) by 615 days.

(21) Appl. No.: 13/507,395

(22) Filed: Jun. 25, 2012

(65) Prior Publication Data
US 2012/0292832 A1 Nov. 22, 2012

Related U.S. Application Data

(60) Division of application No. 11/220,997, filed on Sep. 7, 2005, and a continuation-in-part of application No. PCT/US2004/006908, filed on Mar. 5, 2004.

(60) Provisional application No. 60/677,240, filed on May 3, 2005, provisional application No. 60/452,704, filed on Mar. 7, 2003, provisional application No. 60/463,922, filed on Apr. 18, 2003.

(51) Int. Cl.
*C04B 35/64* (2006.01)
*A61L 27/10* (2006.01)
(Continued)

(52) U.S. Cl.
CPC ............ *A61L 27/10* (2013.01); *A61C 13/0003* (2013.01); *A61F 2/3094* (2013.01); *A61F 2/38* (2013.01); *A61F 2/4425* (2013.01); *A61F 2/4684* (2013.01); *A61F 2002/30133* (2013.01); *A61F 2002/30433* (2013.01); *A61F 2002/30443* (2013.01);
(Continued)

(58) Field of Classification Search
CPC ....... A61L 27/10; A61C 13/0003; A61F 2/28; A61F 2/4425; A61F 2/4684
USPC ................ 264/643, 666, 667, 652; 623/23.56
See application file for complete search history.

(56) References Cited

U.S. PATENT DOCUMENTS

| | | | |
|---|---|---|---|
| 3,314,420 A | 4/1967 | Smith et al. | 623/23.3 |
| 4,067,745 A | 1/1978 | Garvie et al. | 106/57 |

(Continued)

FOREIGN PATENT DOCUMENTS

| | | | |
|---|---|---|---|
| CA | 1154793 | 10/1983 | 261/27 |
| DE | 4434806 A1 | 4/1996 | A61F 2/38 |

(Continued)

OTHER PUBLICATIONS

U.S. Appl. No. 11/220,997, filed Sep. 7, 2005, Serafin, Jr. et al.
(Continued)

*Primary Examiner* — Nahida Sultana
(74) *Attorney, Agent, or Firm* — Christopher John Rudy

(57) ABSTRACT

Prosthetic implant or component therefor of a magnesium oxide stabilized transformation toughened zirconia (Mg-TTZ) ceramic can be made by providing a bisqued initial green body by compressing powder through a cold isostatic press and heating to a bisque stage. Then, without embedding it in an embedding mass, the bisque is machined to have a shape of the same proportions as the shape of, but larger than, the ceramic portion of a fired prosthetic implant or component product. Firing can provide the fired Mg-TTZ ceramic body product.

21 Claims, 23 Drawing Sheets

```
            ┌─────────┐
            │   PSZ   │
            └─────────┘
        ┌─────────┐
        │   TZP   │
        └─────────┘

MONOCLINIC  TETRAGONAL  CUBIC
        ┌─────────┐
        │   TTZ   │
        └─────────┘
```

(51) Int. Cl.
*A61C 13/00* (2006.01)
*A61F 2/30* (2006.01)
*A61F 2/38* (2006.01)
*A61F 2/44* (2006.01)
*A61F 2/46* (2006.01)
*A61F 2/42* (2006.01)

(52) U.S. Cl.
CPC ............... *A61F2002/30492* (2013.01); *A61F 2002/30604* (2013.01); *A61F 2002/30616* (2013.01); *A61F 2002/30714* (2013.01); *A61F 2002/30736* (2013.01); *A61F 2002/30841* (2013.01); *A61F 2002/30843* (2013.01); *A61F 2002/30892* (2013.01); *A61F 2002/30991* (2013.01); *A61F 2002/4205* (2013.01); *A61F 2002/4207* (2013.01); *A61F 2220/0025* (2013.01); *A61F 2220/0041* (2013.01); *A61F 2230/0015* (2013.01); *A61F 2250/0089* (2013.01); *A61F 2310/00239* (2013.01)

(56) References Cited

U.S. PATENT DOCUMENTS

| | | | | |
|---|---|---|---|---|
| 4,081,866 | A | 4/1978 | Upshaw et al. | 623/23.56 |
| 4,279,655 | A | 7/1981 | Garvie et al. | |
| 4,634,561 | A | 1/1987 | DeLuca | 264/17 |
| 4,665,040 | A | 5/1987 | Kurita et al. | 501/105 |
| 4,678,761 | A | 7/1987 | Virkar et al. | 501/104 |
| 4,840,630 | A | 6/1989 | Kitamura | 623/22 |
| 4,885,266 | A | 12/1989 | Hughan et al. | 501/104 |
| 4,888,311 | A | 12/1989 | Davidovits et al. | 501/95.2 |
| 4,939,107 | A | 7/1990 | Ketcham | 501/103 |
| 4,939,996 | A | 7/1990 | Dinkha et al. | 102/501 |
| 4,957,509 | A | 9/1990 | Tamari et al. | 623/16 |
| 4,977,114 | A * | 12/1990 | Horinouchi et al. | 501/104 |
| 5,011,403 | A | 4/1991 | Sadoun et al. | |
| 5,037,438 | A | 8/1991 | Davidson | 623/22.15 |
| 5,082,809 | A * | 1/1992 | Hayashi | 501/105 |
| 5,099,052 | A | 3/1992 | Laine et al. | 556/443 |
| 5,106,303 | A | 4/1992 | Odén et al. | 433/223 |
| 5,112,433 | A | 5/1992 | Dawson et al. | 156/623 R |
| 5,116,376 | A | 5/1992 | May | 623/20 |
| 5,135,154 | A | 8/1992 | Yoshida et al. | 228/46 |
| 5,137,536 | A | 8/1992 | Koshino | |
| 5,139,521 | A | 8/1992 | Schelhas | 623/20 |
| 5,175,132 | A | 12/1992 | Ketcham et al. | 501/103 |
| 5,192,472 | A | 3/1993 | Andersson | 264/40.1 |
| 5,238,742 | A | 8/1993 | Freeman et al. | 428/367 |
| 5,287,698 | A | 2/1994 | Shinzawa et al. | 60/286 |
| 5,290,332 | A | 3/1994 | Chatterjee et al. | |
| 5,336,282 | A | 8/1994 | Ghosh et al. | 51/309 |
| 5,358,529 | A | 10/1994 | Davidson | 623/20.19 |
| 5,358,910 | A | 10/1994 | Atwell et al. | 501/88 |
| 5,358,913 | A | 10/1994 | Chatterjee et al. | |
| 5,411,690 | A | 5/1995 | Ghosh et al. | 264/657 |
| 5,418,298 | A | 5/1995 | Laine et al. | 525/389 |
| 5,453,227 | A | 9/1995 | Rieger | 264/40.1 |
| 5,453,262 | A | 9/1995 | Dawson et al. | 423/593 |
| 5,485,641 | A | 1/1996 | Machmeier et al. | 7/134 |
| 5,549,684 | A | 8/1996 | Amino et al. | 623/20 |
| 5,565,152 | A | 10/1996 | Odén et al. | 264/19 |
| 5,593,719 | A | 1/1997 | Dearnaley et al. | 427/2.26 |
| 5,614,596 | A | 3/1997 | Laine et al. | 525/389 |
| 5,730,928 | A | 3/1998 | Ghosh et al. | 264/639 |
| 5,766,257 | A | 6/1998 | Goodman et al. | 623/20 |
| 5,849,068 | A * | 12/1998 | Hofmann et al. | 106/35 |
| 5,873,725 | A | 2/1999 | Perler et al. | 433/221 |
| 5,919,493 | A | 7/1999 | Sheppard et al. | 425/174.2 |
| 5,922,161 | A | 7/1999 | Wu et al. | 156/272.6 |
| 5,939,147 | A | 8/1999 | Jones | 427/453 |
| 5,958,361 | A | 9/1999 | Laine et al. | 423/592 |
| 5,962,007 | A | 10/1999 | Cooper et al. | 424/426 |
| 5,964,745 | A | 10/1999 | Lyles et al. | 604/891.1 |
| 6,017,839 | A | 1/2000 | Majumdar et al. | 501/104 |
| 6,033,222 | A | 3/2000 | Schneider, II et al. | 433/203.1 |
| 6,044,830 | A | 4/2000 | Jones | 123/670 |
| 6,106,747 | A | 8/2000 | Wohlwend | 264/16 |
| 6,147,135 | A | 11/2000 | Yuan et al. | 523/105 |
| 6,149,073 | A | 11/2000 | Hickey et al. | 239/89 |
| 6,206,927 | B1 | 3/2001 | Fell et al. | 623/20.29 |
| 6,210,443 | B1 | 4/2001 | Marceaux et al. | |
| 6,235,225 | B1 | 5/2001 | Okada et al. | 264/44 |
| 6,302,913 | B1 | 10/2001 | Ripamonti et al. | 623/16.11 |
| 6,303,697 | B1 | 10/2001 | Yuan et al. | 525/240 |
| 6,322,050 | B2 | 11/2001 | Haines | 251/315.04 |
| 6,340,360 | B1 | 1/2002 | Lyles et al. | 604/890.1 |
| 6,344,059 | B1 | 2/2002 | Krakovits et al. | |
| 6,380,113 | B1 | 4/2002 | Kim et al. | 501/105 |
| 6,451,059 | B1 | 9/2002 | Janas et al. | 623/23.51 |
| 6,495,073 | B2 | 12/2002 | Bodenmiller et al. | 264/16 |
| 6,524,345 | B1 | 2/2003 | Valimaa et al. | 623/23.56 |
| 6,558,794 | B1 | 5/2003 | Fehrenbacher et al. | 428/402 |
| 6,629,999 | B1 | 10/2003 | Serafin, Jr. | 623/20.15 |
| 6,634,059 | B2 | 10/2003 | Seiferd | |
| 6,955,716 | B2 | 10/2005 | Xu et al. | 106/35 |
| 7,037,304 | B2 | 5/2006 | Lyles et al. | 604/891.1 |
| 7,250,381 | B2 | 7/2007 | Jaffee | 442/162 |
| 2002/0006532 | A1 | 1/2002 | Robin | 428/697 |
| 2002/0010512 | A1 | 1/2002 | Takei | 623/20.31 |
| 2002/0031675 | A1 | 3/2002 | Cales et al. | |
| 2003/0143350 | A1 | 7/2003 | Jimenez | 428/35.2 |
| 2003/0153984 | A1 | 8/2003 | Khandkar et al. | 623/23.56 |
| 2003/0235738 | A1* | 12/2003 | Zheng | 429/31 |
| 2004/0039450 | A1 | 2/2004 | Griner et al. | 623/20.31 |
| 2005/0149102 | A1 | 7/2005 | Radisch et al. | 606/194 |
| 2006/0015136 | A1 | 1/2006 | Besselink | 606/200 |
| 2006/0025866 | A1* | 2/2006 | Serafin et al. | 623/23.56 |
| 2007/0179041 | A1 | 8/2007 | Muroi et al. | 501/103 |
| 2007/0255392 | A1 | 11/2007 | Johnson | 623/1.15 |
| 2010/0007240 | A1 | 1/2010 | Kornbluh et al. | 310/309 |
| 2010/0055336 | A1 | 3/2010 | Patel et al. | 427/391 |
| 2014/0031949 | A1* | 1/2014 | Serafin, Jr. | 623/23.56 |
| 2015/0053898 | A1* | 2/2015 | Nada et al. | 252/519.1 |

FOREIGN PATENT DOCUMENTS

| | | | |
|---|---|---|---|
| DE | 19930564 A | 10/2000 | ............... B22C 9/12 |
| EP | 00135919 | 5/1984 | ............... C04B 35/48 |
| EP | 0303467 | 2/1989 | ............... A61F 2/38 |
| EP | 0360773 A2 | 3/1990 | |
| EP | 0389461 A | 9/1990 | ............... A61C 5/00 |
| EP | 0477157 A | 3/1992 | ............... A61C 13/00 |
| EP | 0580565 | 1/1994 | ............... A61C 13/00 |
| EP | 0634149 A1 | 6/1994 | |
| EP | 0716839 A1 | 6/1996 | ............... A61F 2/38 |
| EP | 0724868 A1 | 8/1996 | ............... A61F 2/38 |
| GB | 2336317 A | 10/1999 | |
| JP | S55-121970 A | 9/1980 | |
| JP | S57-041942 B2 | 9/1982 | |
| JP | H02-021857 A | 1/1990 | |
| JP | H2-074562 A | 3/1990 | |
| JP | H03-267055 A | 11/1991 | |
| JP | H5-269720 A | 10/1993 | ............... B28B 7/00 |
| JP | H06-351209 A | 12/1994 | |
| JP | H11-228221 A | 8/1999 | ............... C04B 35/46 |
| JP | H11-318961 A | 11/1999 | |
| JP | 2000-504615 A | 4/2000 | |
| JP | 2001-505791 A | 5/2001 | |
| JP | 2001-526573 A | 12/2001 | |
| JP | 2002-47483 A | 2/2002 | |
| JP | 2003-061991 A | 3/2003 | |
| WO | WO 87/02658 A1 | 5/1987 | |
| WO | 92/20634 | 4/1992 | |
| WO | WO 97-30663 A1 | 8/1997 | |
| WO | WO 98/52499 A1 | 11/1998 | |
| WO | WO 01/80917 A2 | 11/2001 | |
| WO | WO 2004/080340 A2 | 9/2004 | |
| WO | WO 2004/080340 A3 | 11/2004 | |
| WO | WO 2004/080340 A3 | 12/2004 | |

OTHER PUBLICATIONS

U.S. Appl. No. 13/507,396, filed Jun. 25, 2012, Serafin, Jr. et al.
U.S. Appl. No. 13/507,397, filed Jun. 25, 2012, Serafin, Jr. et al.

(56) References Cited

OTHER PUBLICATIONS

Notice of Allowance of Jun. 15, 2012 in Canadian Application No. 2,517,623 with allowed claims.
Issued claims of Australian patent No. 2004220540 (Apr. 17, 2008).
Letters of report of Aug. 9 and 15, 2012 for Japanese Application No. 2010-178826, with Jul. 17, 2012 Office action.
Donnelly, L., The Telegraph, "Health warning over hip implants," 9:00 p.m. GMT Jan. 28, 2012, www.telegraph.co.uk/ . . . , 5 pages, printed Jan. 19, 2012.
Patent Abstracts of Japan document for JP Pub. No. 02-074562 (Mar. 14, 1990 A.B.).
McElroy Translation Company, English translation of JP Pub. No. 02-074562 (rec'd Jun. 30, 2011 A.D.).
Letter from JP Associate (Jun. 13, 2011 A.D.) with copy of JP Off. action of May 30, 2011 A.D.
ASTM F 2393-04, 2004, "Standard specification for high-purity dense magnesia partially stabilized zirconia (Mg-PSZ) for surgical implant applications."
Clarke et al., Proc.Instn.Mech.Engrs., 2000, vol. 214 Part H:331-347, "Ultra-low wear rates for rigid-on-rigid bearings in total hip replacements."
Fruh et al., Biomaterials, Jun. 1997;18(12):873-6, Abstract, "Wear characteristics of ceramic-on-ceramic for hip endoprostheses."
Roy et al., Clin.Orthop.Relat.Res., No. 465, pp. 220-226, 2007, "Not all zirconia femoral heads degrade in vivo."
Roy et al., Clin.Orthop.Relat.Res., Feb. 11, 2011, online, Springer, 9 pp., Reduced wear of cross-linked UHMWPE using magnesia—stabilized zirconia femoral heads in a hip.
Roy et al., J.Biomedical Materials Res. Part A., Jun. 21, 2007, online, Wiley InterScience, 7 pp., Phase transformation, roughness, and microhardness of artificially aged yttr.
Stewart et al., J.Arthroplasty, Sep. 2003;18(6):726-34, Abstract, Severe wear and fracture of zirconia heads against alumina inserts in hip simulator studies with microseparat.
Tipper et al., Biomaterials, Aug. 2002;23(16):3441-8, Abstract, Alumina-alumina artificial hip joints, part II: characterization of the wear debris from in vitro hip joint.
Willmann et al., Biomaterials, Nov. 1996;17(22):2157-62, Abstract, "Wear characteristics of sliding pairs of zirconia (Y-TZP) for hip endoprostheses."
Japanese Patent Office, examiner's action of Mar. 9, 2010 in Japanese application No. 2006-509209, with pp. 1-3 of letter of Mar. 24, 2010 from Union Patent Service Center, Inc., Tokyo, Japan, reminder version of May 1, 2010.
Communication of Jan. 11, 2008 in European patent application No. 04718112.8-2310 PCT/US2004/006908, with Supplementary European Search Report.
Examiner's second report on [Australian]patent application No. 2004220540, dated Jul. 13, 2007 A.D.
Examiner's first report on [Australian] patent application No. 2004220540, dated Nov. 20, 2006 A.D.
PCT International Preliminary Report on Patentability of Feb. 2, 2006 (mailed Feb. 16) in PCT/US2004/06908.
Art, annotated drawings sheet, U.S. Pat. No. 4840630.
CeramTec, Biolox® Forte brochure.
I.D.S. filed Jun. 14, 2004, PCT/US2004/006908.
I.D.S. filed Jun. 18, 2004, PCT/US2004/006908.
I.D.S. filed Jan. 13, 2005, PCT/US2004/006908.
International Preliminary Report on Patentability with annex, Jan. 19, 2005, PCT/US2004/006908.
International Search Report with Written Opinion of the ISA, Sep. 10, 2004, PCT/US2004/006908.
Prozyr Biomedical Ceramics, www.prozyr.com page, Oct. 22, 2003.
Serafin, Jr., et al., U.S. Appl. No. 10/717,104, filed Nov. 19, 2003.
Serafin, Jr., et al., U.S. Appl. No. 60/452,704, filed Mar. 7, 2003.
Serafin, Jr., et al., U.S. Appl. No. 60/463,922, filed Apr. 18, 2003.
Serafin, Jr., et al., U.S. Appl. No. 60/677,240, filed May 3, 2005.
Zimmer, Inc., NexGen® System, brochure, 2002.
Espacenet bibliographic data for JP H03195549 (A), Aug. 27, 1991, printed Apr. 28, 2014 (2 pages).
Espacenet bibliographic data for JP H03195550 (A), Aug. 27, 1991, printed Apr. 28, 2014 (2 pages).
Letter of 16th Apr. 2003, w/May 27th reminder page intro., from UPSC UENO Patent Office (5th page redacted) in Japanese application No. 2010-178826, explaining JPO action of Mar. 25, 2013.
Communication of Mar. 5, 2013 in European application No. 13154079-1-1654/2596927.
English translation of EP 0634149 A1 from TranslateMedia, Jul. 29, 2013 A.D.
Communication pursuant to Article 94(3) EPC of Feb. 17, 2014 (Feb. 17, 2014) in European patent application No. 13154079.1-1654 (4 pp.).
Letter of Feb. 26, 2014 from Japanese patent attorney in connection with Feb. 3, 2014 Office Action in Japanese application No. 2010-178826 (pp. 1-5).

* cited by examiner

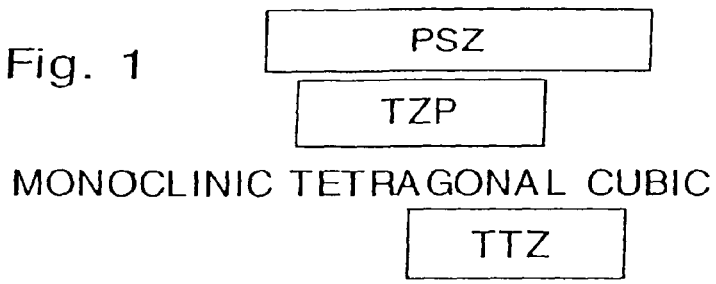
Fig. 1
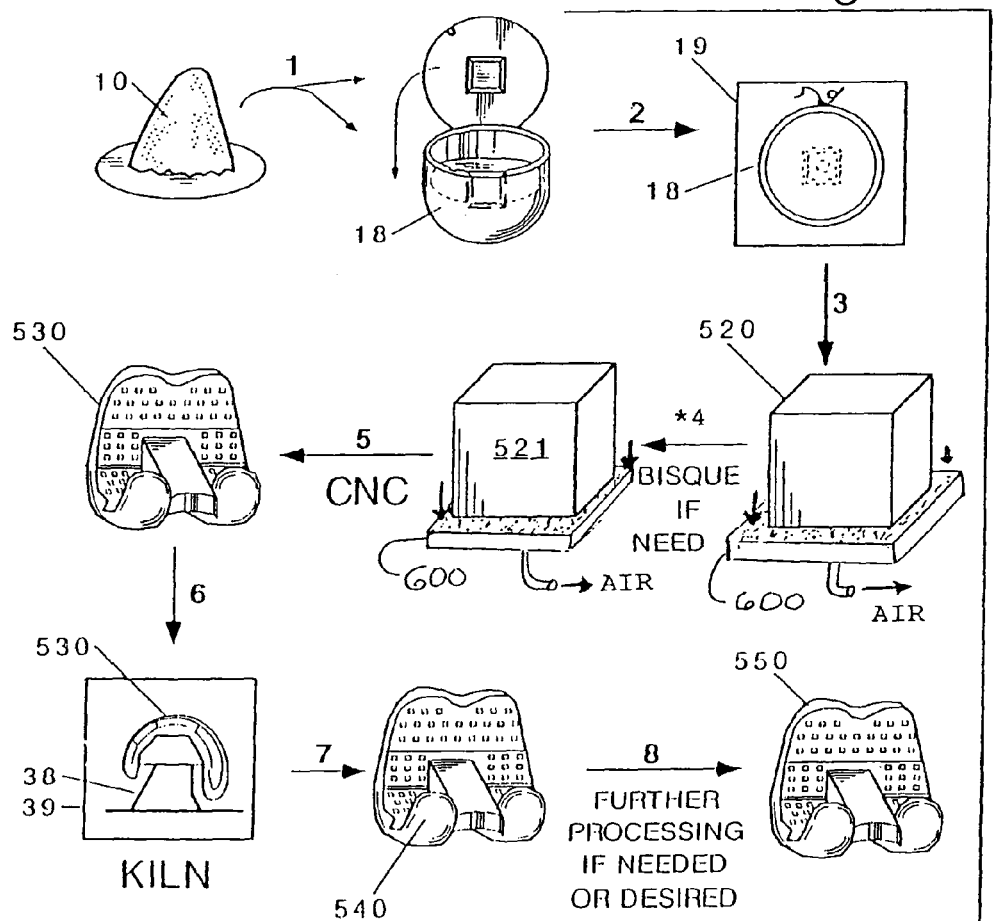
Fig. 2
*ALTERNATE SUB-PROCEDURE:
4A: BISQUE.
4B: 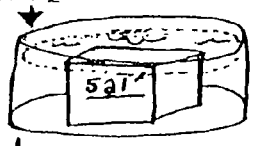 SOAK IN LIQUID ADJUVANT, E.G., PARAFFIN WAX, TO INFILTRATE POROUS BISQUED MATRIX, AND REMOVE.
4C: 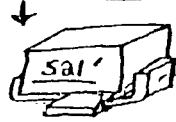 PLACE IN MANUAL CHUCK TO SECURE FOR MACHINING (CNC).

Fig. 27
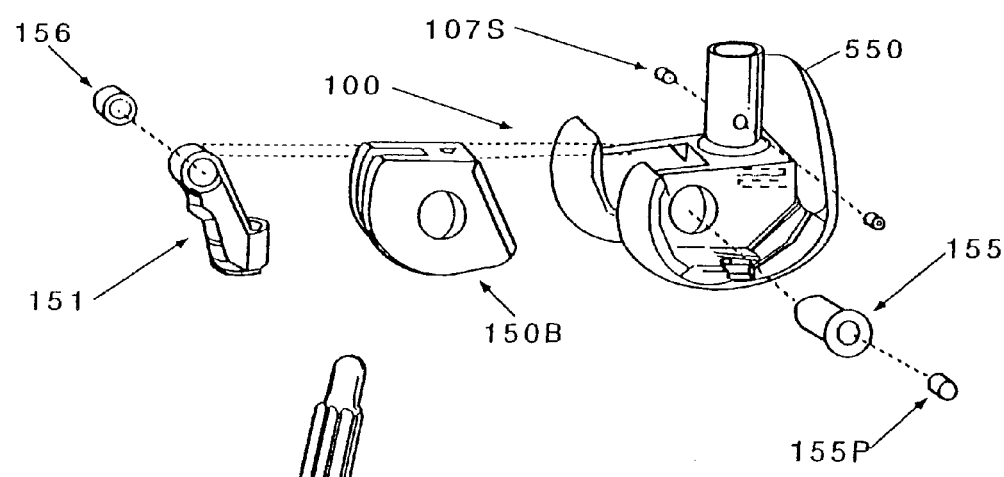
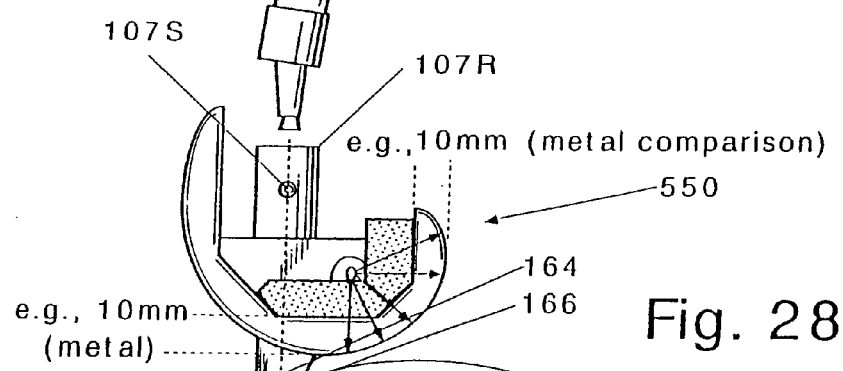
Fig. 28
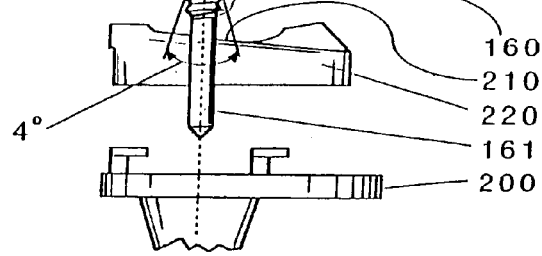

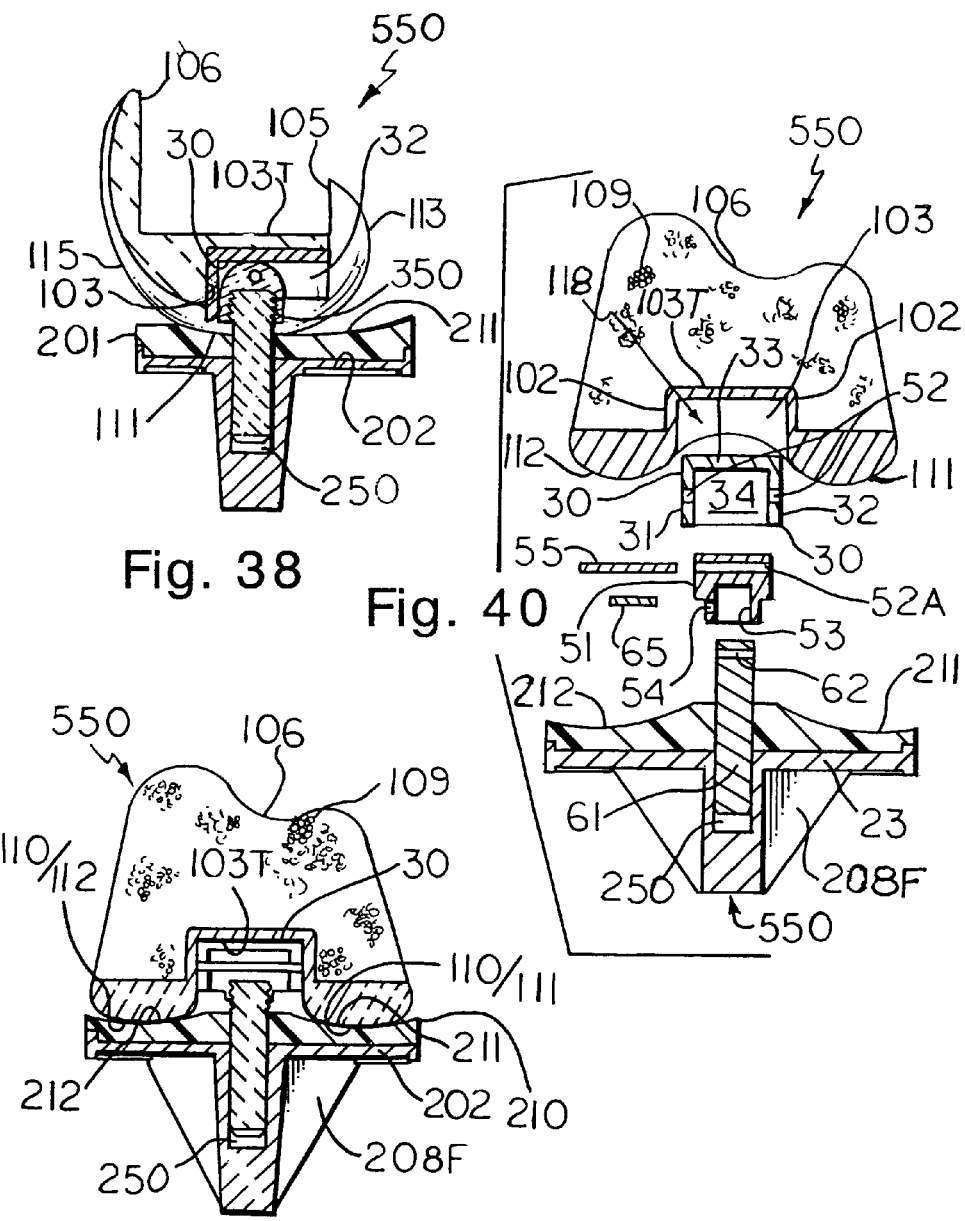

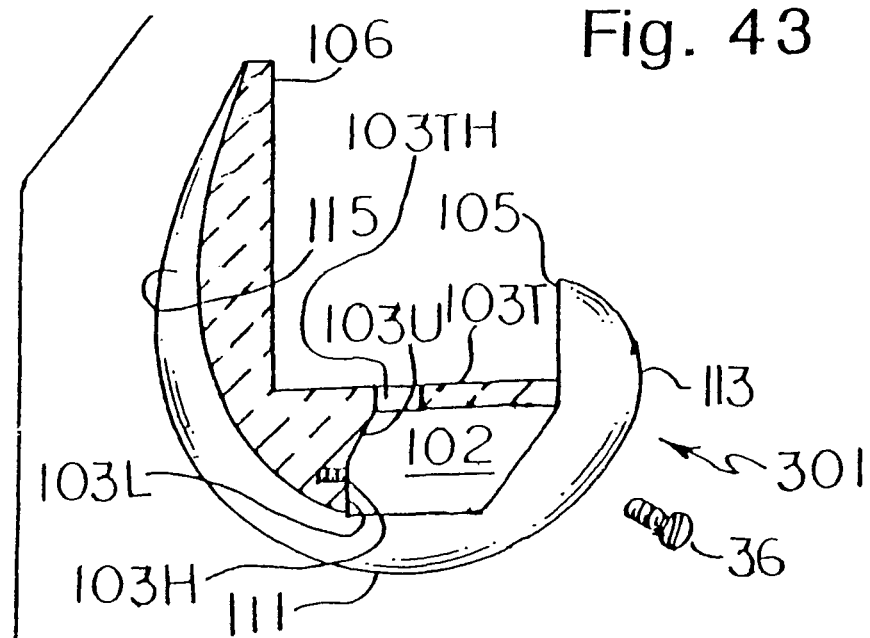
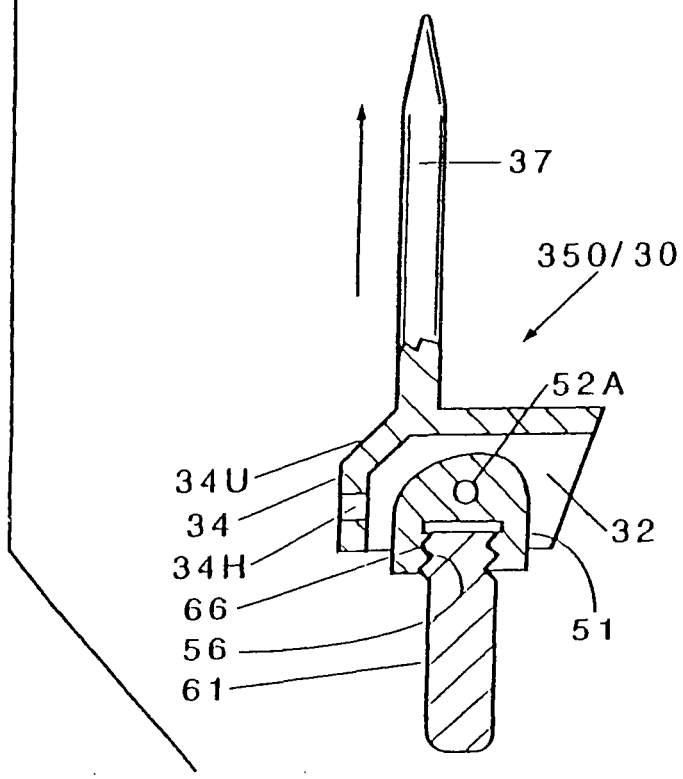
Fig. 43

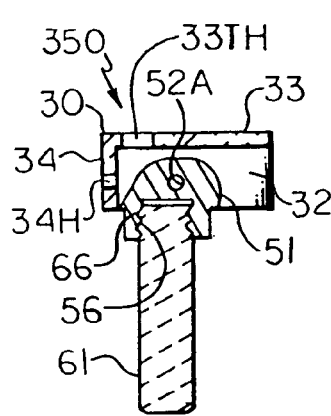
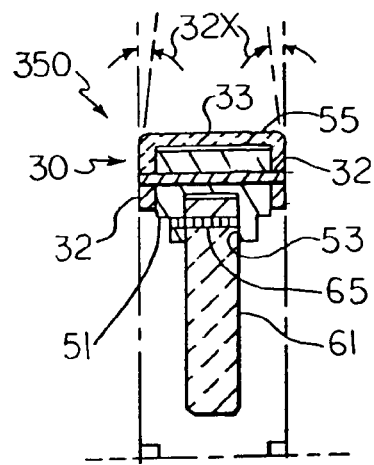
Fig. 45    Fig. 46
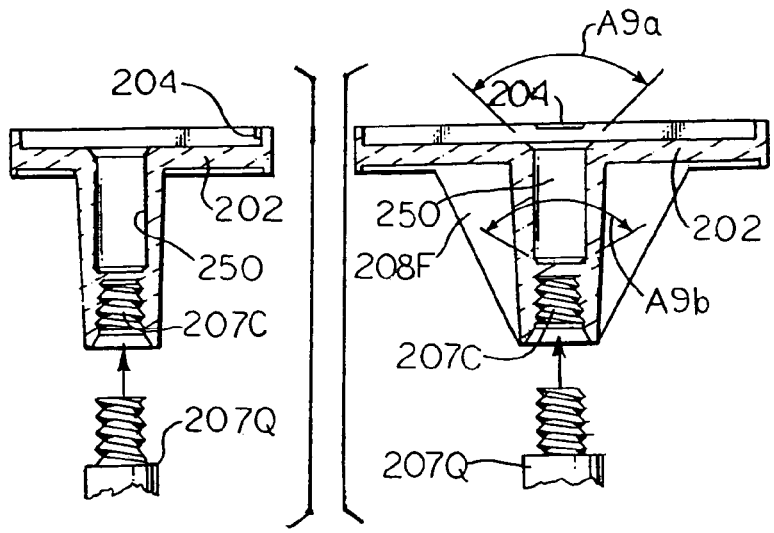
Fig. 47    Fig. 48
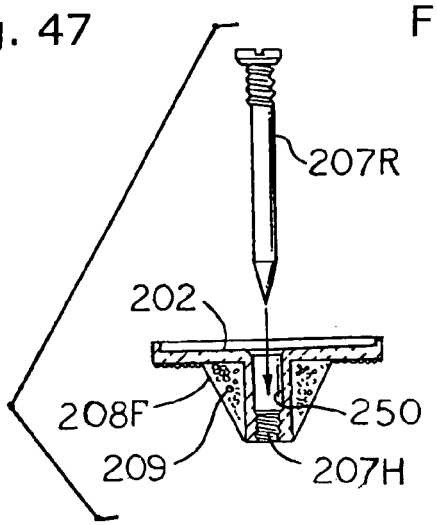
Fig. 49

100CR/550 — 110

100CR/550
117  110

100UK/550
110

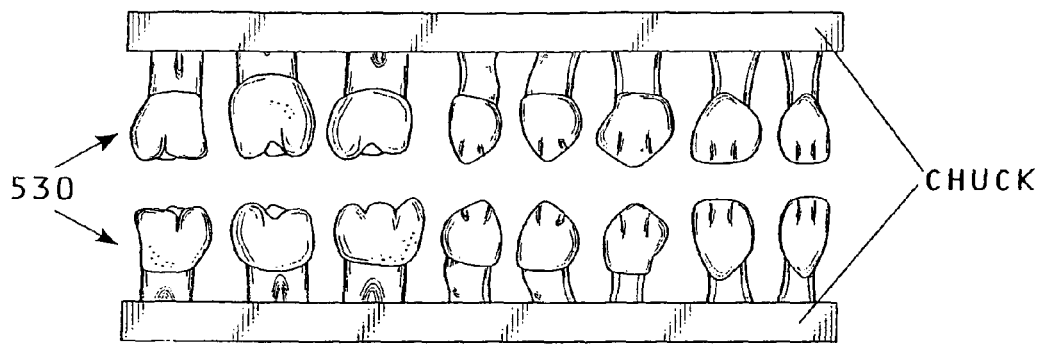
Fig. 65
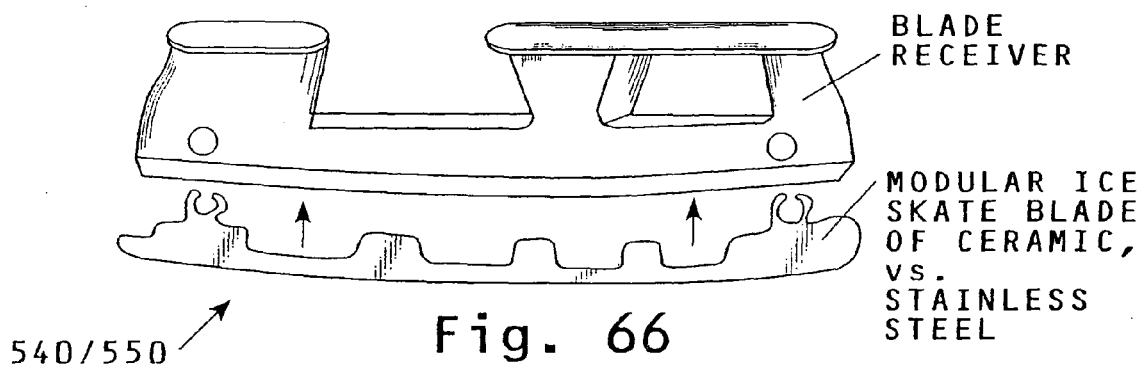
Fig. 66
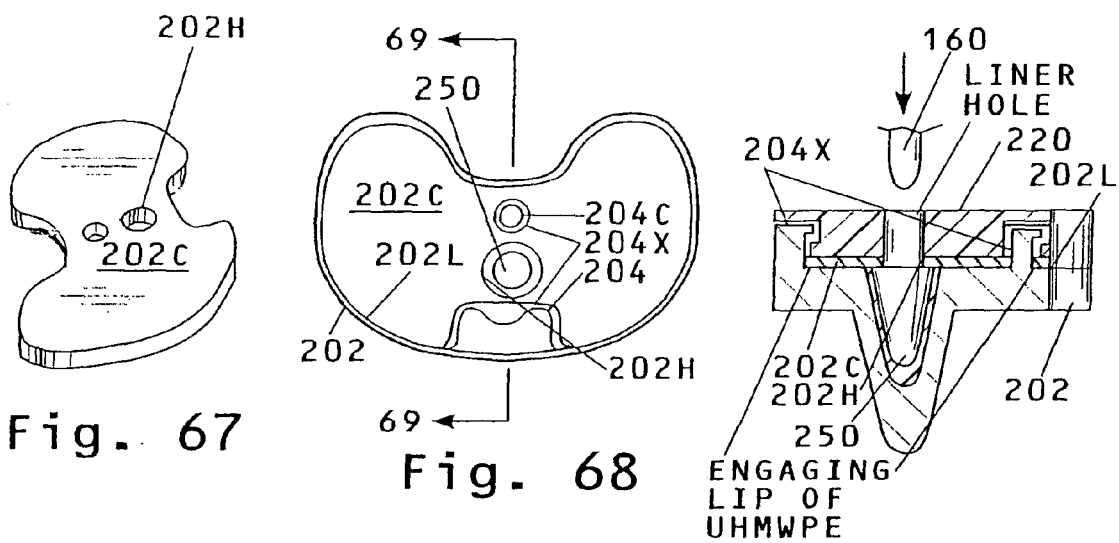
Fig. 67
Fig. 68
Fig. 69

CERAMIC MANUFACTURES

CROSS-REFERENCE CLAIMS OF PRIORITY

This claims the benefits as a divisional of U.S. regular utility patent application Ser. No. 11/220,997 filed on Sep. 7, 2005 A.D., which claims priority benefits of U.S. provisional patent application No. 60/677,240 filed on May 3, 2005 A.D. and is a continuation-in-part of International Patent Application No. PCT/US2004/006908 filed on Mar. 5, 2004 A.D., which, as does the '997 application and the present matter, claims priority benefits of U.S. provisional patent application Nos. 60/452,704 filed on Mar. 7, 2003 A.D., and 60/463,922 filed on Apr. 18, 2003 A.D. The same is claimed under 35 USC 119, 120, 363 and/or 365. The specifications of the abovementioned '997, '240, '908, '704 and '922 applications are incorporated herein by reference in their entireties, which, of course, includes their drawings.

FIELD AND PURVIEW OF THE INVENTION

This invention concerns a method of manufacture of a ceramic body as well as the ceramic body itself. In a particular field, the ceramic body embraces a bodily implant, especially a load-bearing joint implant. For example, the implant may be a femoral knee component in its primary or revisional form, which can be a ceramic posterior stabilized femoral component for a knee implant, and, in another exemplary embodiment, can be an artificial knee implant component made to include ceramic having a rotation device for restraining a femoral component in relation to a corresponding tibial component that can have natural load transfer. Additional ceramic manufactures can be provided.

BACKGROUND TO THE INVENTION

The quest for stronger, more versatile ceramic products is an ongoing, very important concern. Difficulties exist, for instance, in providing sufficiently strong, finished ceramic bodies that would conform to precise and intricate geometries. In light of this, many ceramic products, which would be highly desirable, remain unavailable.

For example, although an alumina femoral knee component is known from Japan, it is made in a manner only to address the most basic of femoral implant designs, and problems with it include its great expense, as it may be made by machining a fired block. Attempts to provide ceramic advanced femoral knee components apparently have met with failure, and such more intricate ceramic implants that require great strength are lacking in the art. As an example of such an implant is a posterior stabilized femoral component for a knee implant. In fact, experts in the art are skeptical that such can be made. Note, too, Amino et al., U.S. Pat. No. 5,549,684.

It would be desirable to overcome such difficulties. It would be desirable, moreover, to provide an efficient and cost effective method to do the same.

In a particularly notable implant provision, Goodman et al., U.S. Pat. No. 5,766,257, discloses an artificial joint having natural load transfer. In a particular embodiment, the joint is a knee. Although it is disclosed that a ceramic substance may be employed, preferably the joint is of metal construction. For example, its femoral component frame is a cast or forged cobalt-chromium alloy, and its tibial component frame is a titanium alloy, with a Co—Cr alloy rotation device and bearings of ultra high molecular weight polyethylene (UHMWPE). See also, Zimmer, Inc., NexGen (Reg. U.S. Pat. & Tm. Off.) System Rotating Hinge Knee Design Rationale, 2002.

Additional modularity may be provided in such a knee implant. See, Serafin, Jr., U.S. Pat. No. 6,629,999.

Employment of ceramic in bodily implants, to include a posterior stabilized femoral component and the knee implants of the '257 and '999 patents as well as other implants could be of benefit. For example, certain patients are allergic to slight amounts of Nickel found in Co—Cr alloys, and ceramic may provide for a hard articulating surface. However, for such complex knee implant components as noted above in particular, a more practical application of the basic concept of employing ceramics is needed.

Serafin, Jr., et al., in WO 2004/080340, the publication of the mentioned '908 application, disclose ceramic manufactures. Therein, a ceramic body can be made by providing an initial green body of ceramic, machining it, and firing it.

Other ceramic making art is known. For example, Bodenmiller et al., in U.S. Pat. No. 6,495,073, disclose a method for the manufacture of medical, dental-medical, dental-technical and technical parts from ceramics. Therein, a powdery raw ceramic is compressed to form a ceramic green compact, and the compact is embedded in an embedding mass, for example, a wax, and machined in the embedding mass. After machining, the part is de-waxed, and fired. Among drawbacks to such methodology, however, is that embedding mass wax can gum up or clog machining tools.

It would be desirable to avoid embedding mass wax in ceramic work, in general, and, in various cases, avoid or limit wax use.

GENERALIZED SUMMARY OF THE INVENTION

In general, the present invention provides, in one aspect, a method for making a ceramic body, which comprises providing an initial green body of ceramic; and machining the initial green body to provide a machined green ceramic body. In the method, in one embodiment, machining the initial green body can be carried out without embedding the initial green body in an embedding mass; in another embodiment, bisquing the initial green body can form a bisqued green body of ceramic, which can be infiltrated with an adjuvant, removed from any gross external adjuvant by which the bisqued green body was contacted for the infiltration, and machined as a removed, infiltrated, bisqued green body. For one instance, the machining may be conducted with the aid of a device that does not provide contact of the initial green body with an attachable substance, for example, machining wax. In such a case, and with the alternative, detailed and even highly detailed ceramic products can be generated without embedding in an embedding mass, and so, avoiding drawbacks associated with the same. The machined green ceramic body may be fired and/or further processed to provide a more finished ceramic body.

Other aspects are the machined green ceramic and more finished ceramic bodies, which may be prepared by the noted method and/or made of certain, particular ceramics. For various illustrations of the many possible, the ceramic body can be a femoral component for a posterior stabilized knee implant, a dental implant or bridge, an ice skating blade, and so forth, which can include a component body for an artificial rotation device containing knee implant prosthesis having a component frame, wherein the rotation device includes a swingable, depending male-type part; the knee prosthesis has a femoral component with condylar articular surfaces, plus the rotation device, and has a tibial component with meniscal articular surfaces that mate with the condylar articular surfaces of the femoral component, plus a rotation device receptacle that includes a female-type part, so that the femoral component is matable to the tibial component through male-female cooperation of the rotation device and the rotation device receptacle, and the knee prosthesis generally has natural load transfer capability by anatomical gliding contact of the condylar and meniscal articular surfaces against one another during anatomical rotation in addition to anatomical flexion and extension.

The invention is useful in providing ceramic items.

Significantly, by the invention, the art of ceramics manufacture is advanced in kind by a unique and highly efficient method. Attachable substances such as machining wax, which often must be removed in later processing steps, can be avoided, and so can embedding be avoided. Many, many types of ceramic bodies can be produced, to include intricate medical and dental implants, and the costs of making these are reduced. Moreover, bothersome or contaminating substances are absent from the machining. In a particularly advantageous embodiment, a vacuum chuck is employed. Thus, strong, finished ceramic bodies which conform to precise and intricate geometries are now available. For further example, a ceramic posterior stabilized femoral knee component with great strength, heretofore unknown to those skilled in the art, is provided. Provision is made for other ceramic bodily implants or implant components, both complex and simple, including other types of femoral knee implant components, single- and multi-piece unicompartmental joint aligning devices, ankle joint condyle-containing components, femoral head balls, humeral shoulder hemispheres, and so forth. Thus, a more practical application of the basic concept of employing ceramics in complex implants such as the knee as generally noted above is provided. In a particular aspect, strong, finished components in rotating device containing knees, which conform to precise, intricate geometries, are made available, and component bodies for an artificial rotation device containing knee prostheses made of zirconia ceramics are hereby advantageously provided, for femoral and/or tibial components. Other types of ceramic bodies are made available such as gears, flow-control fittings, and so forth. Certain zirconia ceramic bodies are most advantageously provided.

Numerous further advantages attend the invention.

DEPICTION OF SEVERAL EMBODIMENTS OF THE INVENTION

The drawings form part of the specification hereof. With respect to the drawings, which are not necessarily drawn to scale, the following is briefly noted:

FIG. 1 shows a graph illustrating general phases of zirconia ceramics.

FIG. 2 shows a scheme of manufacture with the invention.

Figure 9:
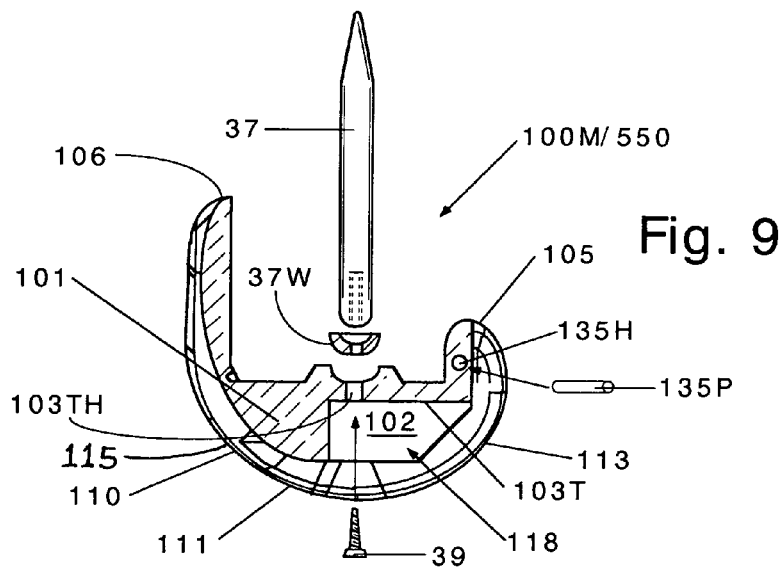
FIGS. 9-15 show some other finished ceramic bodies hereof, embodied as follows.

FIG. 9. A modular ceramic knee implant with a metal intramedular femoral post and metal securing washer, with a metal screw fastener, also with a metal or ceramic peg for a posterior stabilizing stop, shown from one side in partial section.

Figure 10:
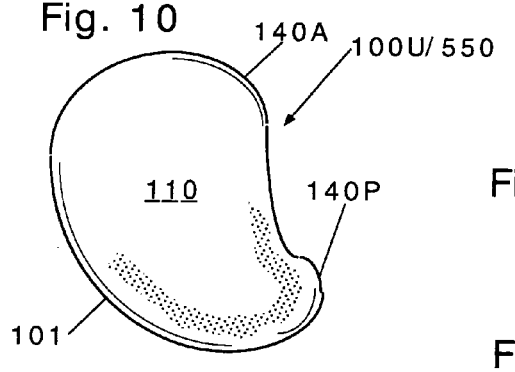
Figure 11:
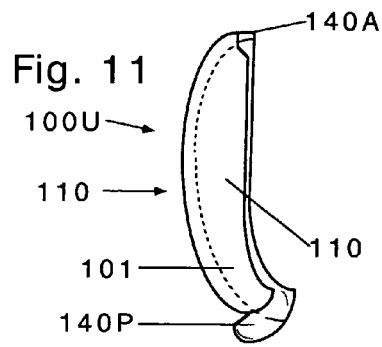

FIGS. 10-11. A one-piece unicompartmental knee joint spacer as a plan view (FIG. 10) and side view (FIG. 11).

Figure 12:
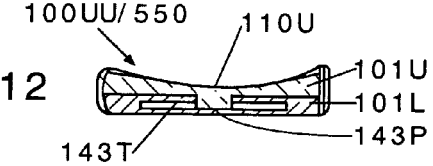
Figure 13:
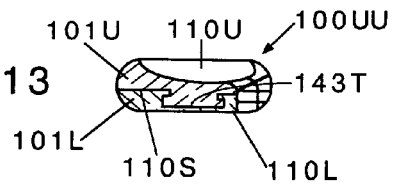
Figure 14:
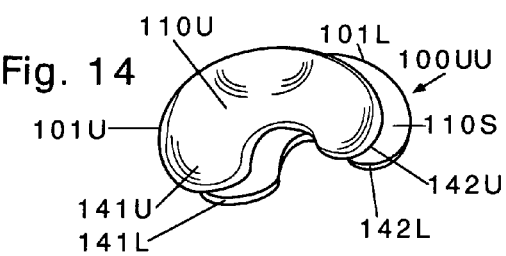

FIGS. 12-14. A two-piece unicompartmental knee joint aligning device, shown as a side sectional view (FIG. 12); a side sectional view (FIG. 13) taken perpendicularly to the view of FIG. 12, and a top view (FIG. 14) in a sliding engagement mode.

Figure 15:
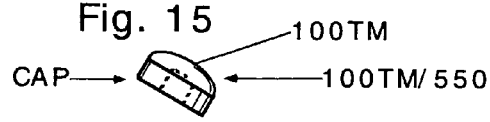

FIG. 15. A temporal mandibular joint implant cap.

Figure 16:
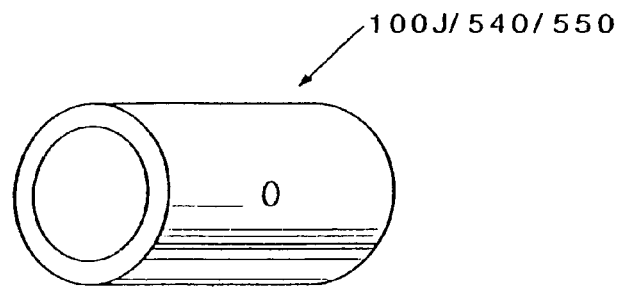

FIGS. 16-19 show other finished ceramic bodies, embodied as industrial apparatus, components, or devices, as follows:

FIG. 16. An industrial bearing, shown in perspective.

Figure 17:
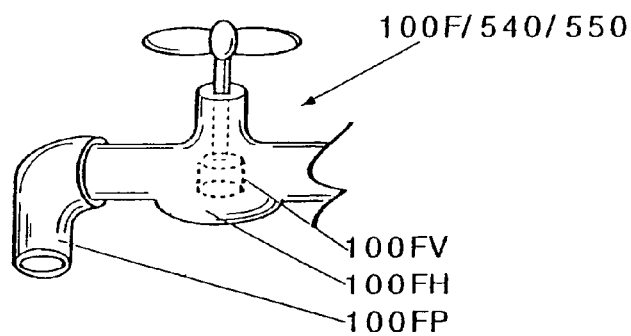

FIG. 17. Flow control apparatus, shown in plan.

Figure 18:
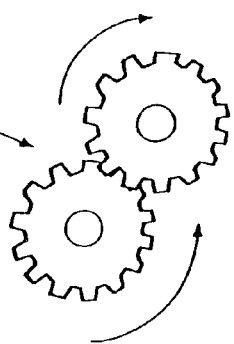

FIG. 18. A set of gears, shown in elevation.

Figure 19:
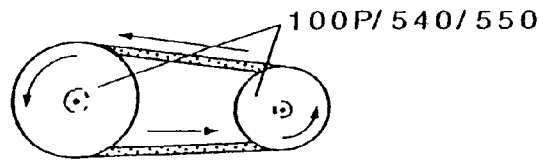

FIG. 19. A set of pulleys, shown in elevation.

Figure 20:
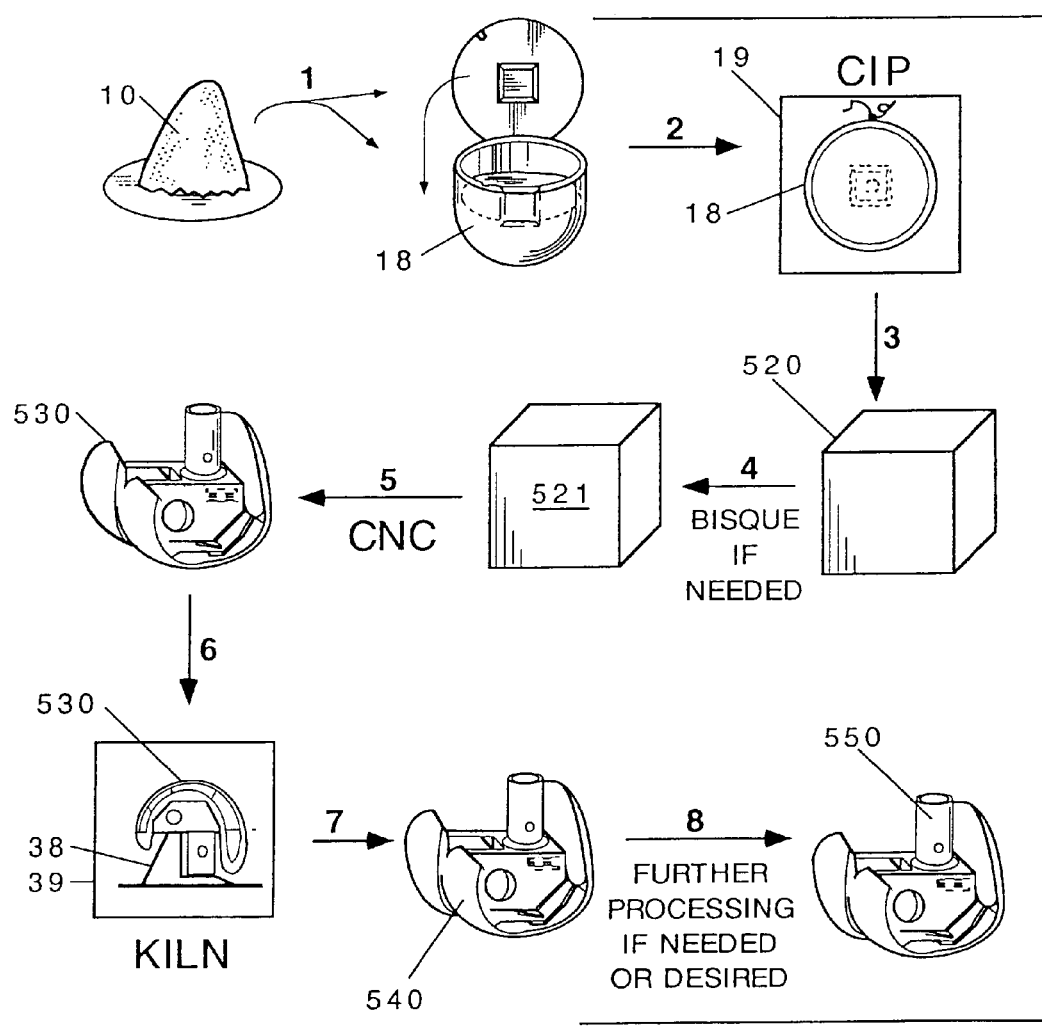

FIG. 20 shows a scheme of manufacture with the invention to make another ceramic body, here a finished base component for an artificial prosthetic knee joint implant, which will contain a rotation device. Compare, FIG. 2.

Figure 21:
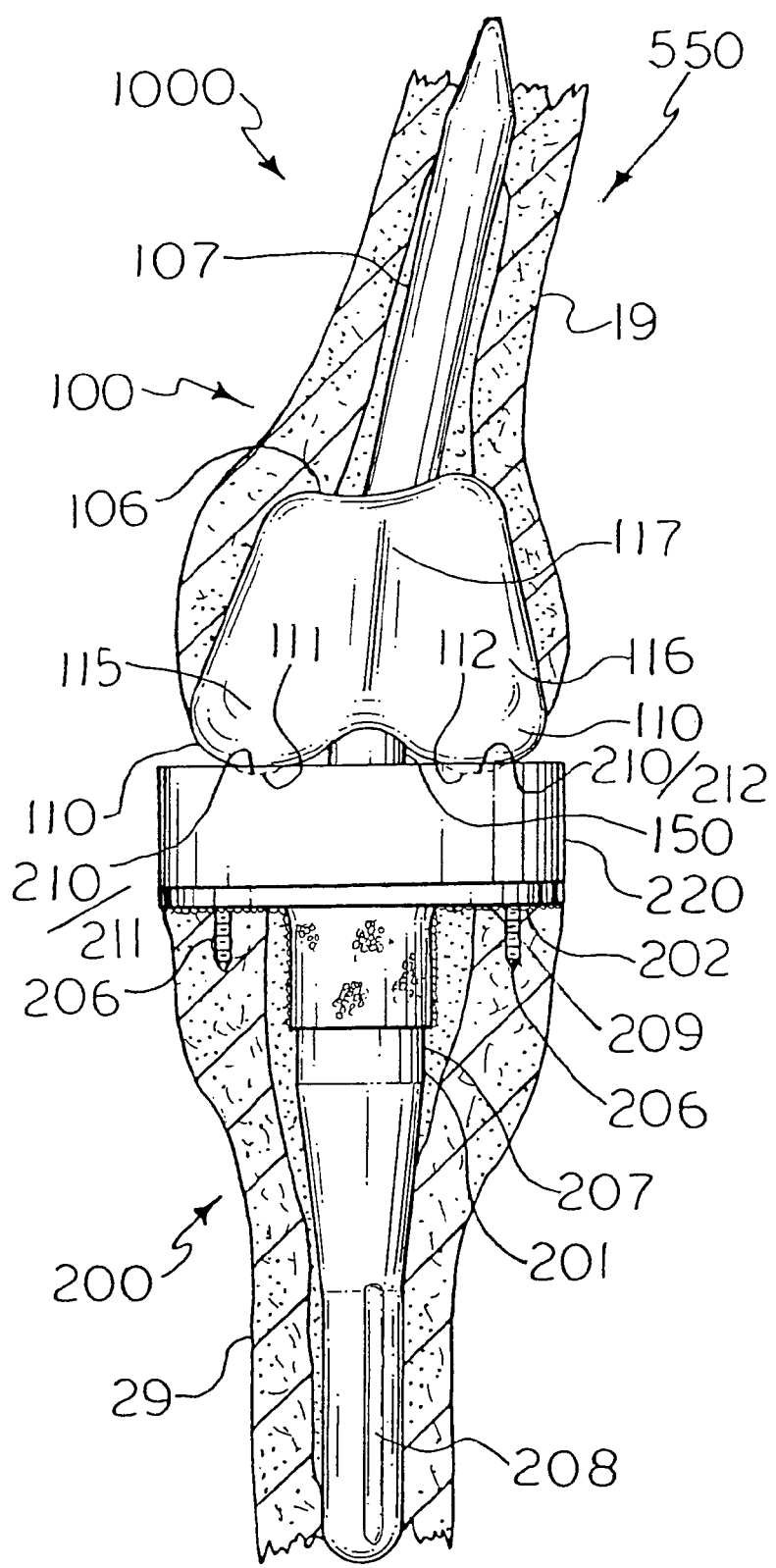

FIG. 21 is a front (anterior to posterior direction) of an artificial, prosthetic knee joint implant that may have at least a ceramic component body among its femoral and tibial components such as the base femoral component body shown in FIG. 20, which contains a rotation device.

Figure 22:
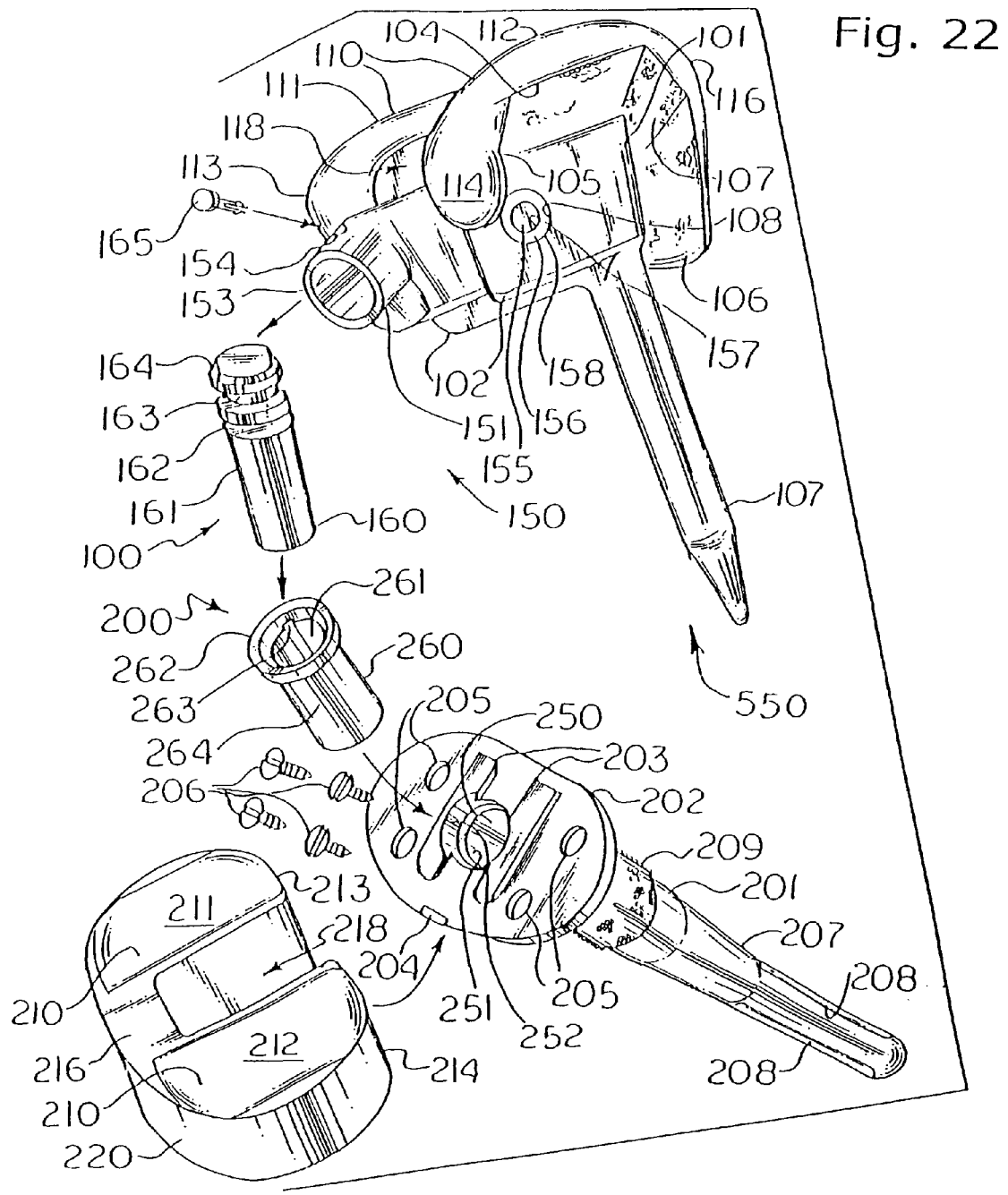

FIG. 22 is an exploded view of the joint of FIG. 21.

Figure 23:
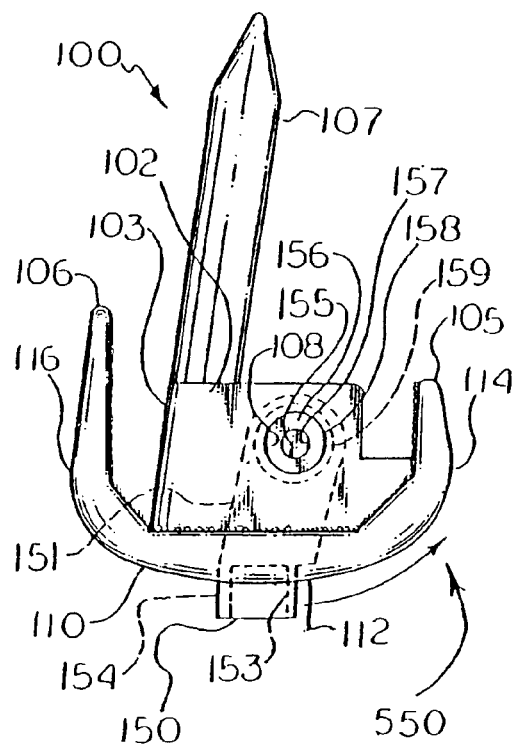

FIG. 23 is a left side view (lateral to medial direction) of the femoral component to the joint of FIGS. 21 and 22.

Figure 24:
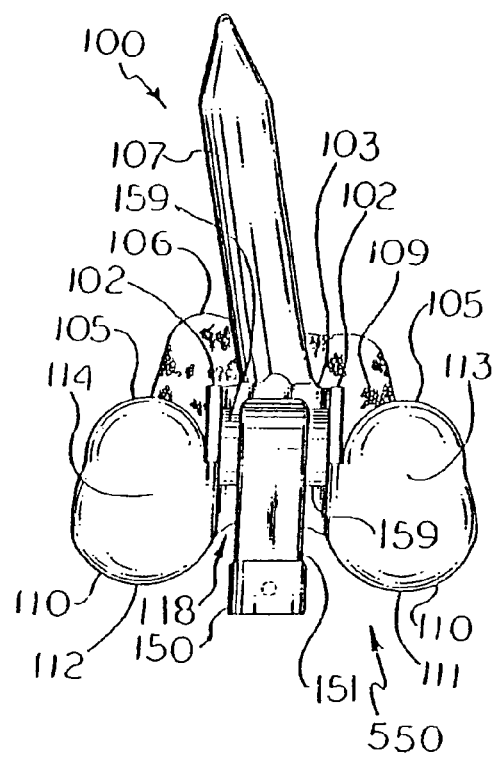

FIG. 24 is a rear view (posterior to anterior direction) of the femoral component of FIG. 23.

Figure 25:
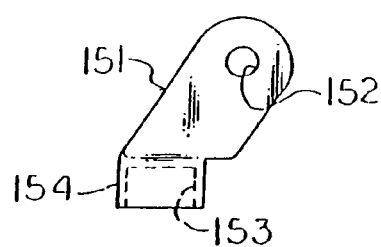

FIG. 25 is a left side view of the rotation device member of the femoral component in FIGS. 22-24.

Figure 26:
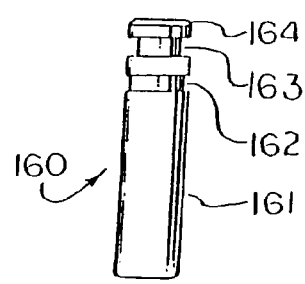

FIG. 26 is a side view of the rotation device femoral-tibial taper pin of the joint as seen in FIG. 22.

FIG. 27 is an exploded, perspective view of a femoral component of another artificial, prosthetic knee joint of the invention containing a rotation device and having a ceramic body.

FIG. 28 is an exploded, side view of the prosthetic knee joint having the femoral component of FIG. 27.

Figure 29:
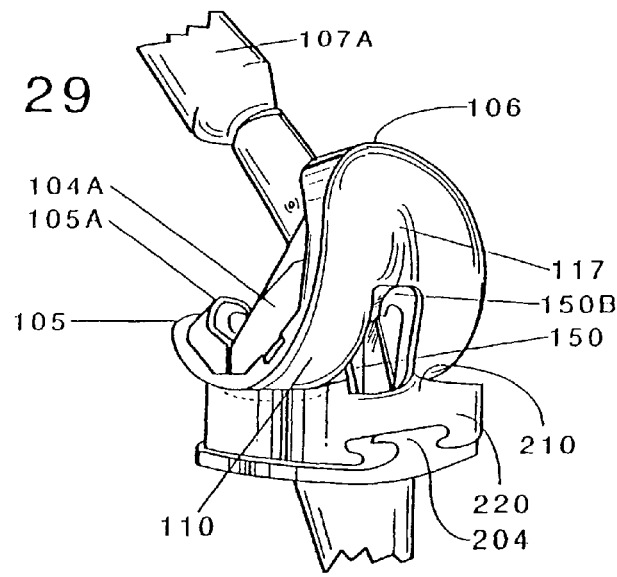

FIG. 29 is a front, perspective view of the joint of FIG. 28, assembled and having several augments to accommodate bone loss in place in its femoral component.

Figure 30:
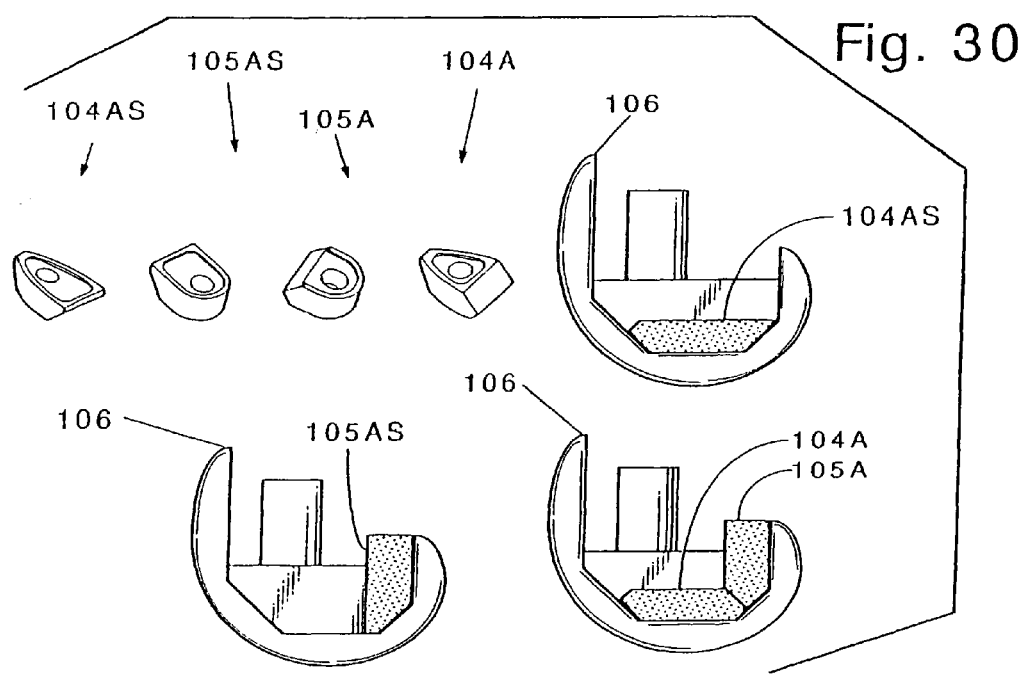

FIG. 30 shows perspective and side views illustrating various femoral augments, some of which can be seen within FIG. 29.

Figure 31:
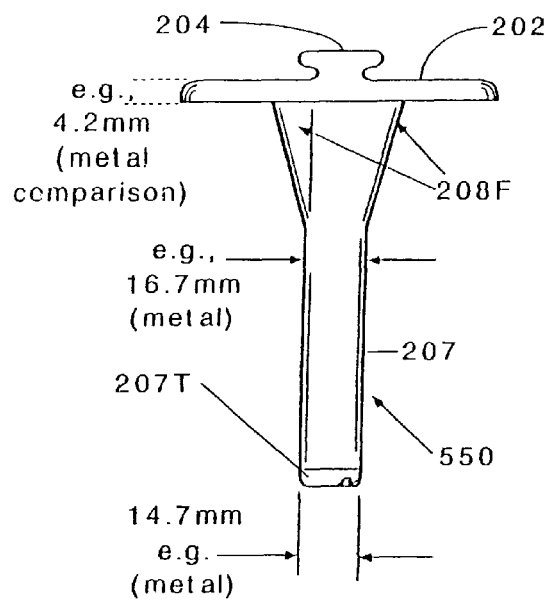

FIG. 31 is a side view of the tibial base plate found within the joint of FIG. 28.

Figure 32:
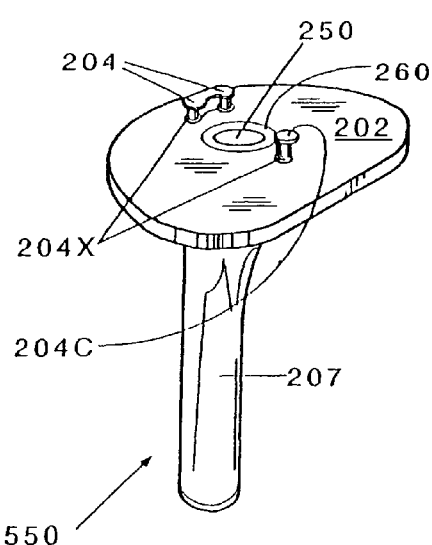

FIG. 32 is a top, perspective view of the tibial base plate of FIG. 31.

Figure 33:
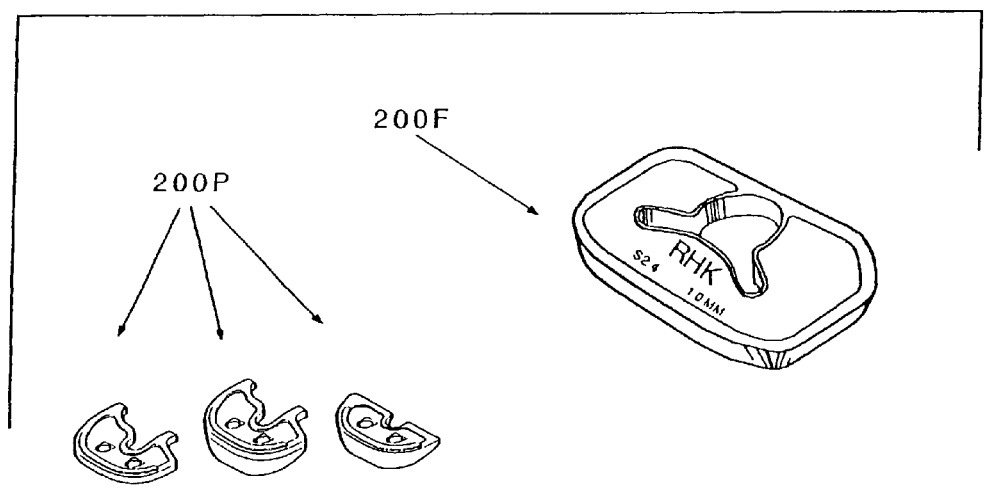

FIG. 33 is a perspective view of some partial tibial augments that may be employed with the tibial base plate of FIG. 31.

Figure 34:
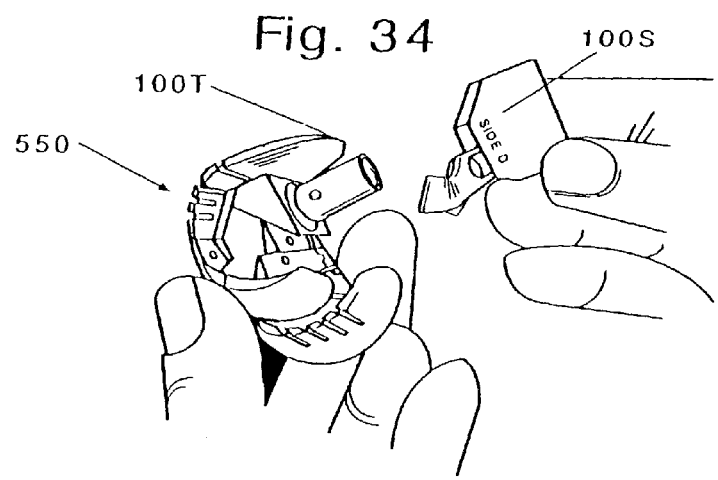

FIG. 34 is a perspective view of a ceramic provisional femoral component having a modular rotation device employed for fitting the patient to a femoral component such as that of FIG. 27 with a properly sized rotation device.

Figure 35:
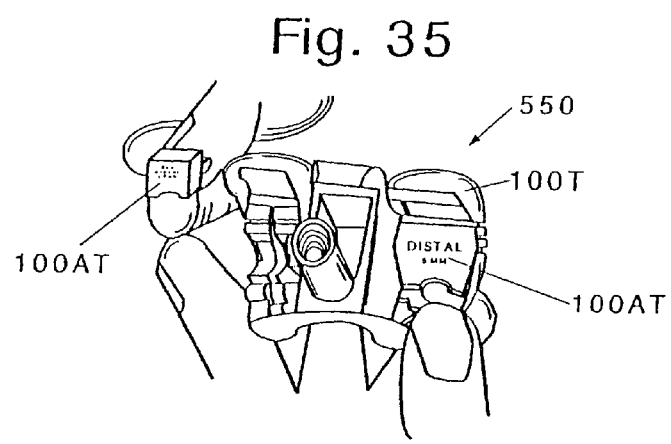

FIG. 35 is a perspective view of a ceramic provisional femoral component having snap-in augments employed for fitting the patient to a femoral component such as that of FIG. 27 with augments as may be necessary to make up for a lack of bone. The augment provisional components snap into the femoral provisional component.

Figures 36, 37:
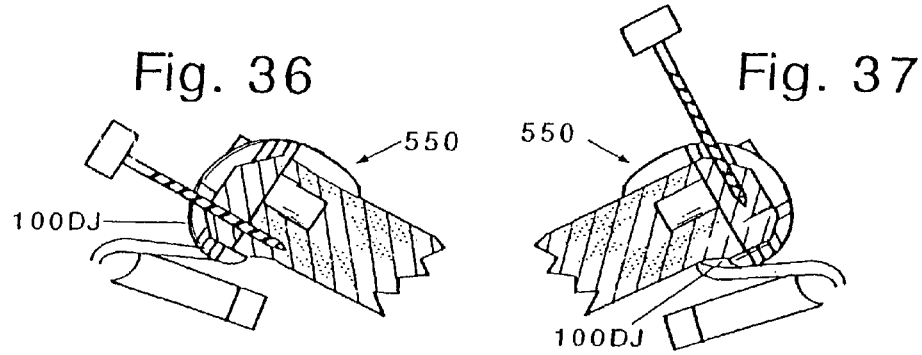

FIGS. 36-37 show side views of a ceramic femoral provisional cutting guide for implantation of a femoral component such as that of FIG. 27 with drilling, as follows:

FIG. 36. In a proximal direction into resected femur.

FIG. 37. In a posterior direction into resected femur.

FIG. 38 is a saggital sectional view of a modular ceramic human knee joint of the invention.

FIG. 39 is a rear, section view of the joint of FIG. 38.

FIG. 40 is an exploded, rear sectional view of a modular ceramic knee joint of the invention, similar to that of FIGS. 38 and 39, employing pin type attaching of its axial (taper) pin.

Figure 41:
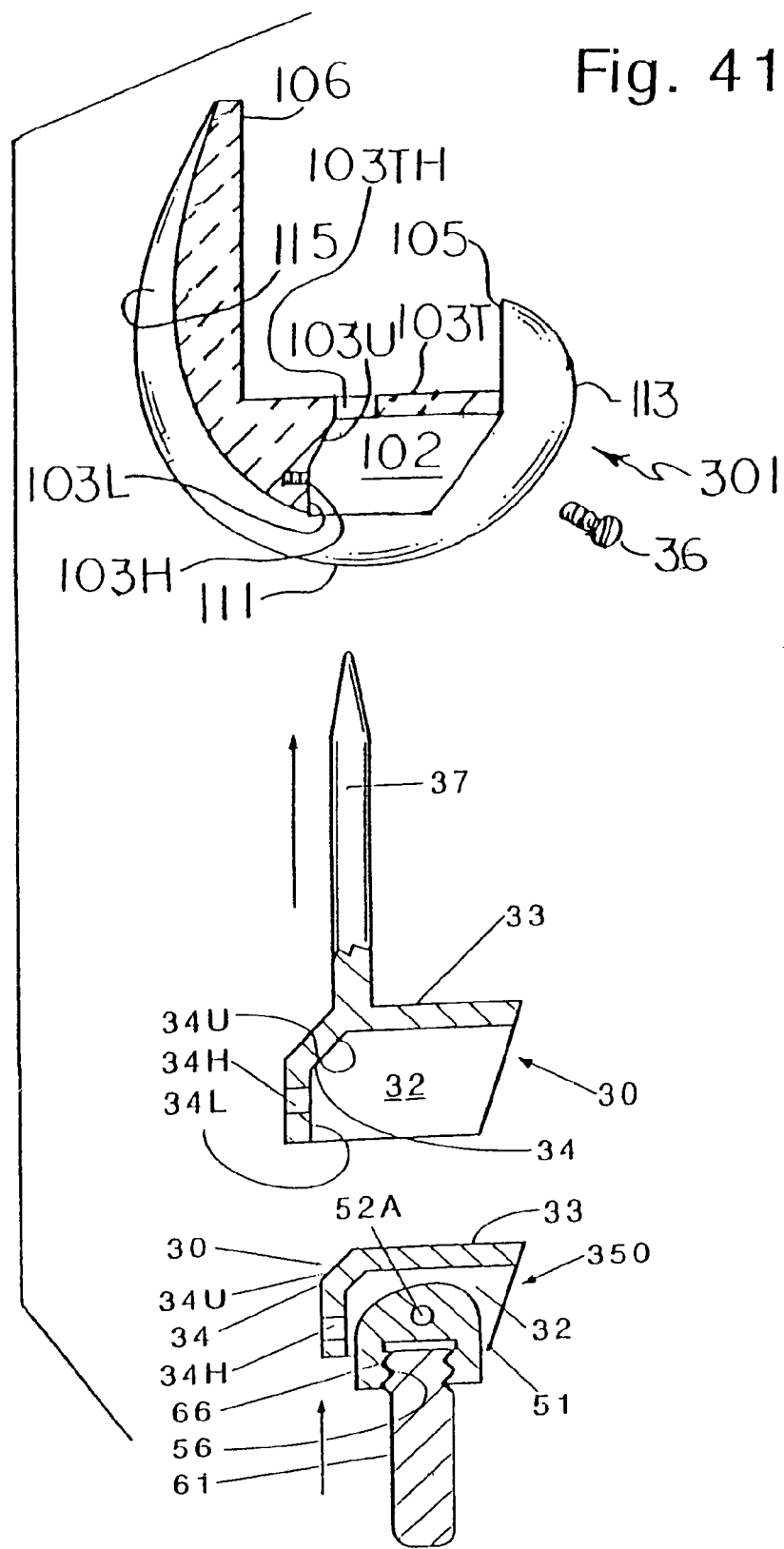
Figure 42:
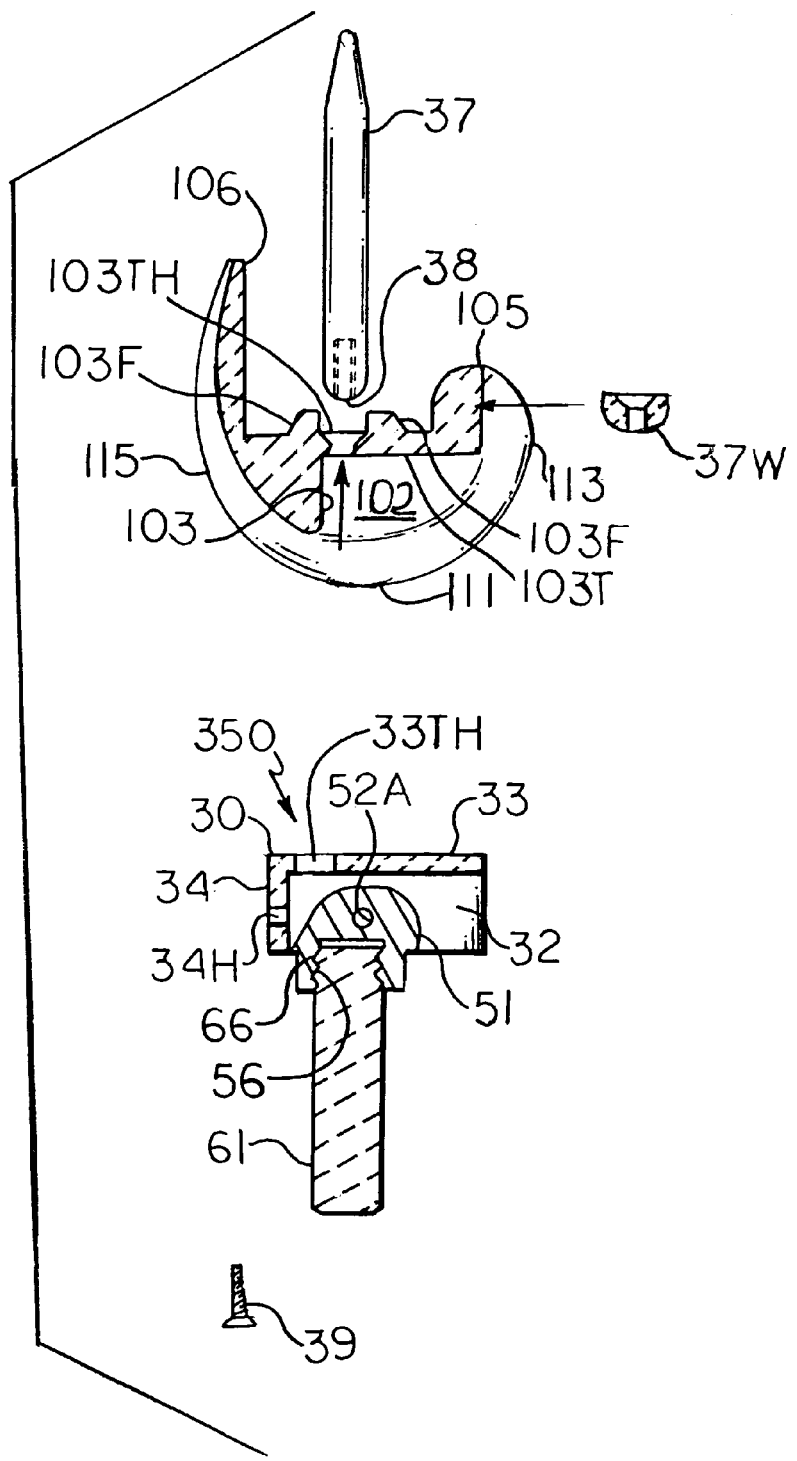

FIG. 41-43 show exploded, saggital sectional views of ceramic femoral knee components with modularity, as follows:

FIG. 41. Module-in-module.

FIG. 42. Top-insert stem.

FIG. 43. One-piece box with stem, plus a rotation device added thereto.

Figure 44:
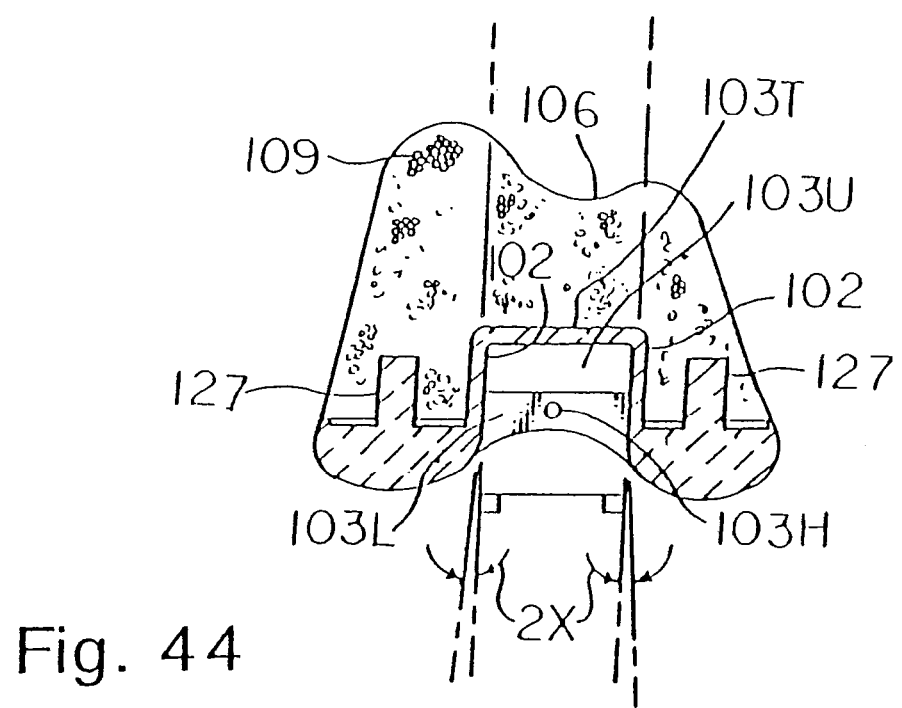

FIG. 44 is a rear sectional view of the femoral component frame of FIGS. 41-43.

FIG. 45 is a saggital sectional view of the insertable rotation device with a swingable, depending male type part of the modular joint of FIGS. 38 and 40.

FIG. 46 is a rear sectional view of the insertable rotation device of FIG. 45.

FIG. 47 is an exploded side view of another embodiment of a modular ceramic tibial tray of the invention.

FIG. 48 is an exploded rear view of the tray of FIG. 47.

FIG. 49 is an exploded rear view of another embodiment of a modular ceramic tibial tray of the invention.

Figure 50:
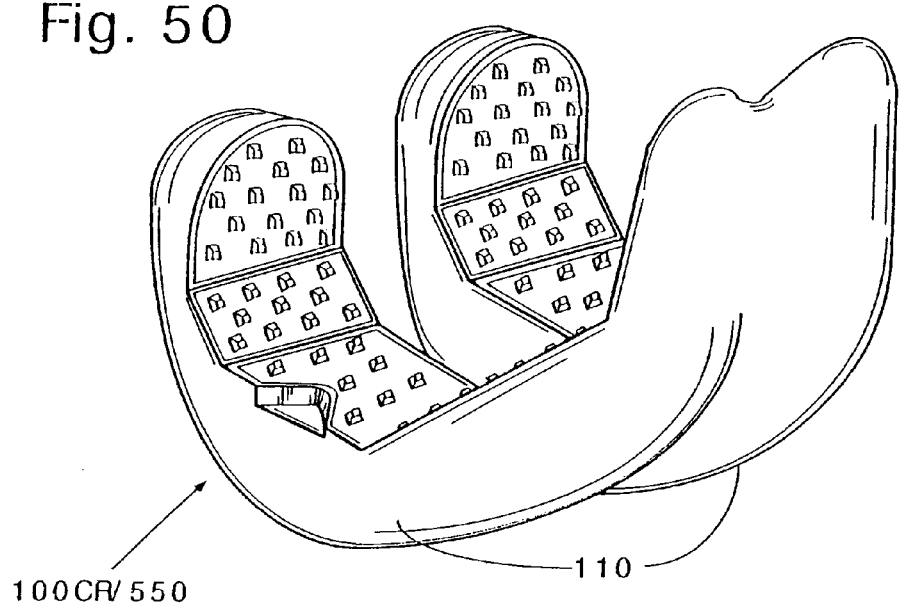
Figure 51:
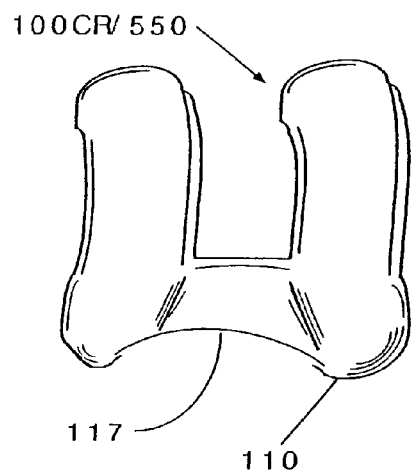

FIGS. 50-51 show views of a zirconia ceramic cruciate-retaining femoral component implant for a left human knee implant, as follows:

FIG. 50. Left, front, perspective plan view.

FIG. 51. Bottom view.

Figure 52:
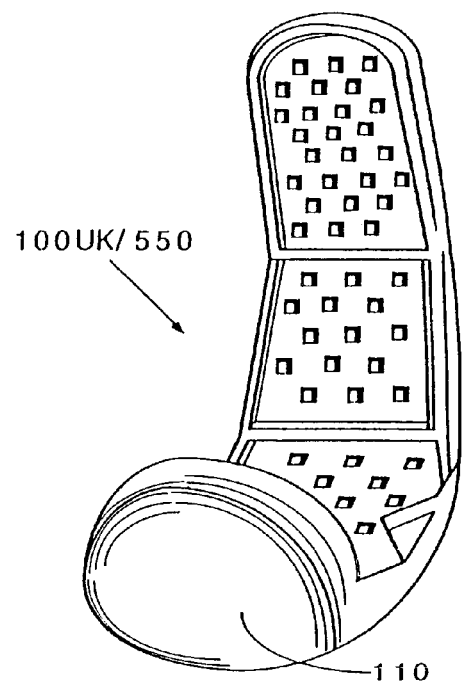

FIG. 52 is a rear, perspective view of a ceramic, unicompartmental femoral component condylar implant.

Figure 53:
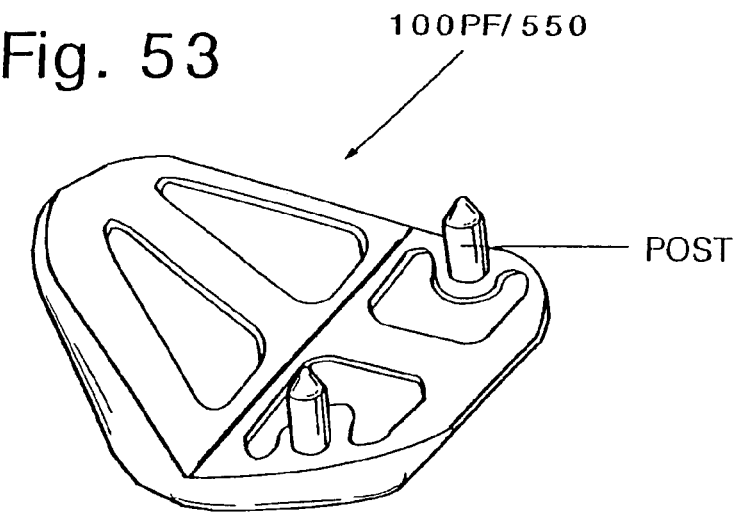
Figure 54:
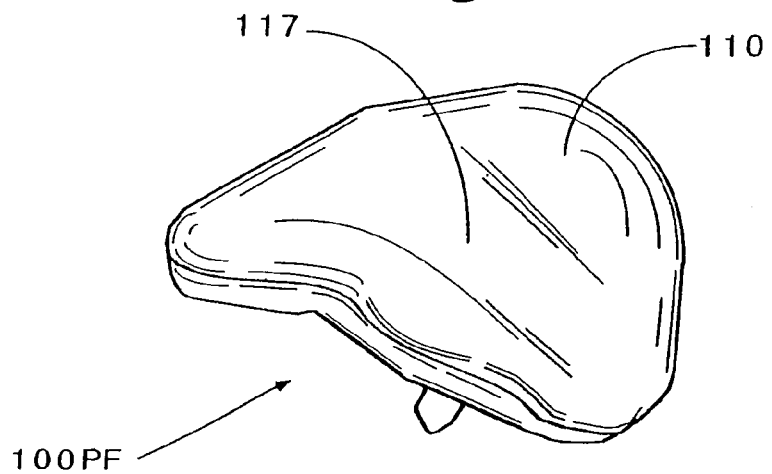

FIGS. 53-54 show views of a ceramic patellofemoral joint implant for a left human knee, as follows:

FIG. 53. Top, rear perspective.

FIG. 54. Front perspective.

Figure 55:
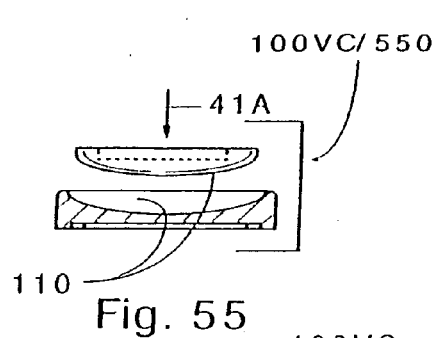
Figure 56:
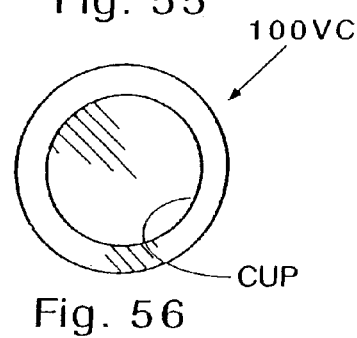

FIGS. 55-58 show views of inter-spinal vertabra ensembles for implantation in adjacent, facing vertebral bodies for replacement of a disc, embodied as follows:

FIGS. 55-56. Cap or cup mounting style, shown as a side, exploded view, with one component in section (FIG. 55); and a top view taken along arrow 41A (FIG. 56).

Figure 57:
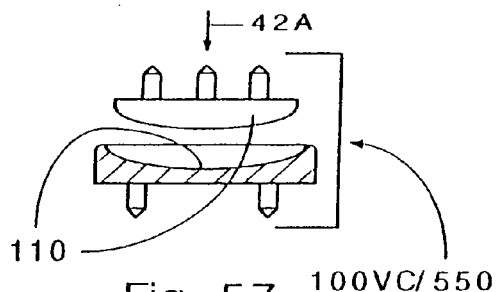
Figure 58:
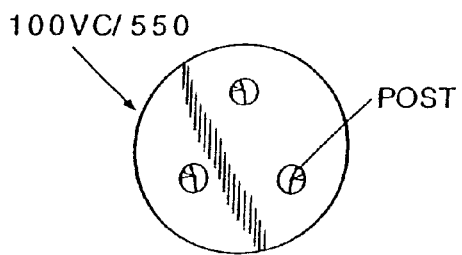
Figures 59, 60:
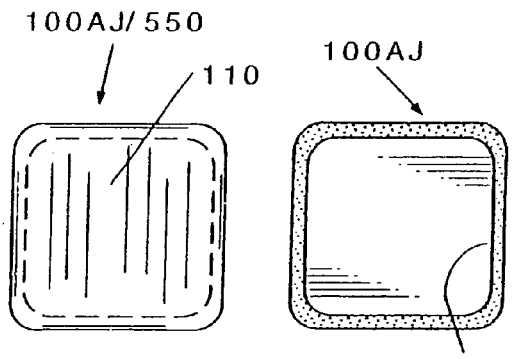
Figures 61, 62:
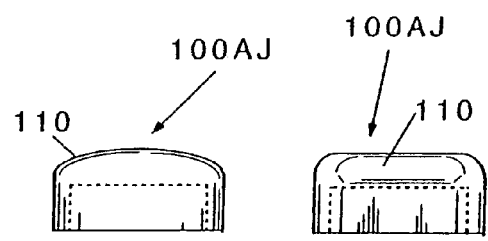

FIGS. 57-58. Peg or post mounting style, shown as a side, exploded view, with one component in section (FIG. 57); and a top view taken along arrow 42A (FIG. 58).

Figure 63:
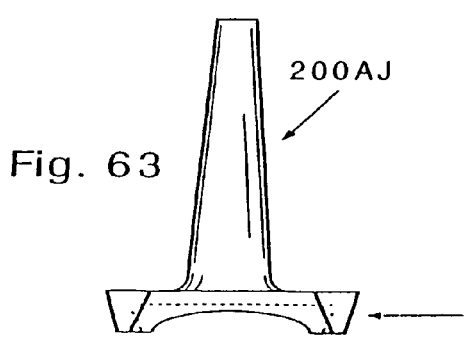
Figure 64:
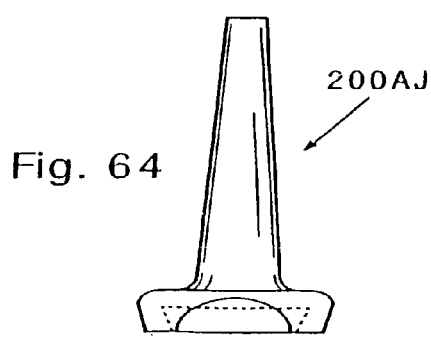

FIGS. 59-64 show views of an ankle implant ensemble, with FIGS. 59-62 a talus cap, which may be a hemi-implant, shown in top (FIG. 59); bottom (FIG. 60); side (FIG. 61); and front (FIG. 62) views; and with FIGS. 63-64 a tibial tray, shown in side (FIG. 63) and front (FIG. 64) views.

FIG. 65 shows in more detail machining of an initial green body of ceramic that is held with a vacuum and/or manual chuck, said body embracing teeth.

FIG. 66 shows a ceramic ice skate blade makable hereby.

FIGS. 67-69 show views of a ceramic intermediary articulation plate for a tibial tray and liner, with FIG. 67 showing the plate; FIG. 68 a top view of the plate mounted in the tray; and FIG. 69 a sectional view of the assembled plate, tray and liner, taken along 69-69 in FIG. 68.

DETAIL FURTHER ILLUSTRATING THE INVENTION

The invention can be further understood by additional detail, especially to include that which is set forth below, which may be read in view of the drawings. Such is to be taken in an illustrative and not necessarily limiting sense.

In general, in accordance with the practice of the present invention, a ceramic body can be made by providing an initial green body of ceramic, and machining the initial green body to provide a machined green ceramic body. The machined green ceramic body may be fired and/or further processed to provide a more finished ceramic body.

In certain embodiments of the present invention, one or more parts to one or more components of the knee joint implant is made of ceramic. Preferably, at least the basic femoral component with its condylar articulating surfaces is made of ceramic. Typically the ceramic condylar articulating surfaces articulate with a corresponding tibial tray liner made of ultra high molecular weight polyethylene (UHMWPE). Other parts of the femoral and tibial components may be made of, or to include, ceramic.

In certain other embodiments hereof, various additional articles of manufacture may be made. These include ceramic.

The ceramic may be any suitable type. Among these may be mentioned ceramics from "A" to "Z," to include alumina to zirconia, and mixtures thereof. A representative ceramic may be a boride, carbide, nitride, oxide, silicate and so forth of Al, Si, Sc, Y, La, the lanthanide series elements, Ac, the actinide series elements, Ti, Zr, Hf, V, Nb and/or Ta and so forth and the like. A ceramic may be toughened; thus, for example, an alumina may be a toughened alumina as known in the art. Preferably, the ceramic is a zirconia ceramic. The ceramic may be stabilized, and any suitable stabilizer may be present in any suitable amount. For example, the zirconia ceramic may generally be a partially stabilized zirconia (PSZ) which is a zirconia ceramic stabilized, for example, with about three to three and one half percent by weight magnesium oxide, or with about from four to five percent by weight yttrium oxide, and which exists in a phase that may in essence span or be selected from tetragonal and/or cubic phases; and, from among the PSZ ceramics, a magnesium oxide stabilized transformation toughened zirconia (Mg-TTZ), which is a zirconia ceramic stabilized with approximately three to three and one half percent by weight magnesium oxide and which exists to a substantial extent in a tetragonal phase; or a yttrium oxide tetragonal zirconia polycrystalline (Y-TZP), which is a zirconia ceramic stabilized with approximately three mole percent yttrium oxide and existing to include in a tetragonal phase. Compare, FIG. 1.

The finished ceramic may contain other substances. For example, zirconia ceramics typically contain a small amount of hafnia ceramic substances, say, about two percent by weight, owing to the fact that Hf is found with Zr in nature and is difficult to remove from Zr. This, however, need not be, and frequently is not, detrimental.

Beneficially, the ceramic is the Mg-TTZ, especially for prosthetic implants, and those which are load bearing and/or are joint replacement parts or components, the ceramic is the Mg-TTZ, to include for reasons of its good hardness and toughness, and its excellent resistance to heat- and/or water-induced reversion toward a monoclinic phase. For example, a general comparison of alumina, Y-TZP and Mg-TTZ can be made as follows:

Strength after firing: Y-TZP>Mg-TTZ>alumina.

Strength after autoclaving: Mg-TTZ>alumina>Y-TZP.

Assigning arbitrary strength numbers to these ceramics for purposes of further illustration may yield the following values:

After firing: Y-TZP (150); Mg-TTZ (125); alumina (100).

Post-autoclave: Mg-TTZ (125); alumina (95); Y-TZP (50). Thus, it may be said that Mg-TTZ does not revert to a monoclinic phase through the in vitro action of hot water, or it is not degraded or attacked by water. With in vivo use, the following has been generally observed with respect to wear for alumina and Y-TZP implanted femoral hip balls:

At 1-4 years retrieval: Y-TZP better than alumina.

At 5-8 years retrieval: Y-TZP and alumina nearly same.

At 9-10, or more years: Alumina better than Y-TZP.

Accordingly, in vivo, Mg-TTZ, known, for example, to have been implanted as femoral hip balls (with bores drilled after firing), should be observed to provide better short and/or long term wear than alumina and better long term wear than Y-TZP.

Desirably, the ceramic body initially is made from a micropowder and/or nanopowder. For instance, a zirconia ceramic may be made from monoclinic zirconia powder with an about from 0.5-micron (um) to 10-um cross-section, as a micropowder, or with an about from 1-nanometer (nm) to 500-nm cross-section, as a nanopowder, which micropowder or nanopowder may contain about from two to five percent by weight magnesium oxide as a stabilizer. Preferably, the zirconia powder has an about from 1-um to 2-um cross-section, as the micropowder, or an about from 15-nm to 450-nm cross-section, as the nanopowder, and contains about from 3.1 to 3.4 percent by weight magnesium oxide.

The initial green body of ceramic can be provided by any suitable method or process. Pressure molding is preferred to make the initial green body, especially by a cold isostatic press (CIP) technique. Thus, a powdered ceramic material is fed into a cavity of a high-pressure press, and formed under pressure into the initial green body. A binder may be employed if needed or desired. Typically, a binder is employed with the ceramic powder if it is a micropowder or larger size. It may be the case that a binder is not required for the initial green body of nanopowder.

The initial green body of ceramic is made to have a suitable density. Generally, the density of the initial green body is at least about twenty percent of the theoretical density for that ceramic. Preferably, the density of the initial green body is at least about thirty percent of theoretical, and more preferably at least about fifty percent of theoretical. Some may consider that higher theoretical densities of the initial green bodies may be provided by the employment of the smaller powders, others not, which may depend on the material. (Nanopowders, however, may sinter better than larger powders.) Higher theoretical densities may be provided by higher pressure, and so forth.

The initial green body may be provided in any suitable shape. Convenient shapes can include cylinders, tetrahedra, triangular prisms, rectangular or cubic blocks, regular pentagonal prisms, and so forth. Advantageously, the initial green body of ceramic is provided as a rectangular or cubic block.

For machining, certain initial green bodies may be left raw and pressed, and others may require heating to provide a bisque, which is considered to be a form of an initial green body. Thus, certain ceramic powders such as a zirconia nanopowder may be machined in a raw, pressed state. Certain other ceramic powders such as a micropowder for conversion into Mg-TTZ are bisqued. The heating required to form a bisque generally is considered mild. For example, a zirconia micropowder may be bisqued at temperatures about from one hundred to one thousand or eleven hundred or more degrees C., for about from one to ten hours.

In the practice of the invention, the initial green body is machined to provide the machined green ceramic body. Machining can be by any suitable method, to include by hand, by lathe, by drilling, cutting, and so forth, but preferably is carried out with a multi-axis precision cutting or tooling machine, for example, a computerized numerical control (CNC) machine. Generally, temperatures during the machining can be ambient temperatures. The machined green ceramic body may have any suitable shape, but preferably has a shape which is a precursor shape, analogous in most essential aspects, to the shape of any finished ceramic body. In light of this, the present method has a significant advantage that the machined green body may be provided with a complex shape so that if a finished ceramic would be made from it, minimal transformation to the essential shape of the body occurs. Thus, such asymmetrical, complex geometries as those of femoral components for a knee, to particularly include revisional femoral knee implant components, are readily gained. Other complex geometries, as illustrations of the versatility of the invention, in the field of surgical implants may include knee joint implant tibial components, unicompartmental knee joint aligning devices of one or more pieces, ankle joint implant components, spinal components, temporal mandibular joint implants, and so forth. Of course, other bodies can be made as the machined green body, including surgical implants such as hip femoral heads, shoulder humeral hemispheres, and so forth, which can advantageously include any trunnion receiving bores provided in precursor form so that the machined green body has less symmetry than an uninterrupted ball or generally planarly truncated ball (uninterrupted hemisphere), i.e., symmetry of a C-infinity point group, to include hip femoral and shoulder humeral heads with trunnion-receiving, tapered, truncated frustoconical bores, or a shape more asymmetric than C-infinity. And so, for additional examples, complex geometries of the femoral component and/or its rotation device and/or an insertable spike, and the tibial component tray and/or an insertable spike are readily gained.

The machined green ceramic body, as a precursor to a finished ceramic body, is provided suitably larger than the finished ceramic body. Thus, typically depending on the density of the machined green ceramic body and the density of the finished ceramic body, the machined green ceramic body may be about from one half to eighty percent larger than the corresponding finished ceramic body, in many cases about from ten to thirty percent larger. With the zirconia ceramics and Mg-TTZ in particular, typical undersizes of the more finished ceramic in relation to the machined green body made from micropowder run about from fifteen to twenty-five percent, to include about from sixteen to twenty-three percent, less than the size of the finished ceramic body. In other words, an eighteen percent undersized more finished ceramic based on the controlling size of the machined green body may be considered to be equivalent to an about one hundred twenty-two percent oversized machined green body in relation to the controlling size of the more finished ceramic body. Thus, the relationship (I) generally obtains:

$$\text{Oversize \%} = (100\%/(100\% - \text{undersize \%}))(100\%). \quad \text{I.}$$

For example, a more finished ceramic body which is twenty percent undersized from a machined green body, is made from the machined green body which is 1.25 times as large (125%) as the more finished ceramic body.

Preferably, the more finished ceramic body is provided. This can be accomplished through at least one heating step.

The more finished ceramic body can be provided through firing of the machined green body. The firing may be conducted at any suitable temperature, for instance, within ranges about from one thousand to three thousand degrees C., for any suitable time. A temperature gradient leading to the firing temperature in the ceramic body is preferred, to include as may be conducted within ranges of about from one half to twenty degrees per minute. Annealing of the fired piece may immediately follow the firing, which may be carried out at any suitable temperature, for instance, within ranges about from seven hundred to one thousand eight hundred degrees C., for any suitable time. Further ceramic processing can include hot isostatic press (HIP) action, as may be desired or pertinent to certain ceramics. The fundamentals and practice of such procedures in general are known to those skilled in the art. Of course, details may vary for any ceramic.

For example, a Mg-TTZ more finished ceramic body may be made by firing a correspondingly larger machined green body in an oven at about from one thousand six hundred to one thousand nine hundred degrees C., preferably about from one thousand seven hundred to one thousand eight hundred degrees C., for about from one to four hours, say, about from two to three hours, with ramping temperatures leading to the firing temperature increasing from room temperature to the firing temperature at a suitable rate, say, about from one to two degrees C. per minute. After such firing, annealing is desirably carried out by gradually cooling the body from the firing temperature, keeping it in a heated condition, for example, by gradually reducing the temperature of the hot, fired body about from two hundred to five hundred degrees C., say, about three hundred fifty degrees C., below the firing temperature of the body, and holding the body at the annealing temperature for about from one to three hours, say, about two hours. Cooling from the annealing temperature may be carried out at any suitable rate, say, at a rate similar to, but the reverse of, the ramping rate, until the annealed ceramic body is about room temperature. Such generally provides the more finished Mg-TTZ ceramic body, which typically has a density which approaches or attains theoretical density. Advantageously thus, no further heat processing such as by HIP action on the fired and annealed Mg-TTZ ceramic body is typically required.

A Y-TZP more finished ceramic body may be made by firing the correspondingly larger machined green body in an oven about from one thousand three hundred to one thousand five hundred degrees C. for a body made from micropowder, or about one thousand one hundred to one thousand three hundred degrees C. for a body made from nanopowder. Ramping, annealing and cooling procedures can be, in general terms, analogous to those for the Mg-TTZ ceramic. However, cooling at about from seven to ten degrees C. per minute, down to heat treating temperature, may be advantageously employed. Finally, HIP action under Argon or Nitrogen, say, Argon, at about from one thousand to three thousand pounds per square inch (psi) pressure, at a temperature about from one thousand to two thousand degrees C., for a cycle time about from four to twenty-four hours, with final cooling to room temperature. Thus, the finished ceramic body may be relieved of inorganic and organic substances, and approach or attain theoretical density.

Appropriate kiln furniture can be employed. Such furniture is beneficially placed in non-critical parts of the body. For example, the femoral knee joint implant component may be placed upside down in the kiln on kiln furniture that touches portions of the prosthesis that form a bone-implant interface rather than being placed right side up to have its articulating condylar surfaces touched during firing.

The finished ceramic parts and components can be dense materials. Generally, the finished ceramic should be at least about ninety percent of theoretical density, or it may be at least about ninety-five, ninety-six, ninety-seven, ninety-eight, or ninety-nine percent of theoretical density. Desirably, the density of the finished ceramic approaches, and especially attains, theoretical density.

The more finished ceramic knee body may be further processed as desired or required. Typically, any further processing is of a minor nature, particularly when compared to what would otherwise be required to provide the final shape from machining a fired ceramic block. Thus, polishing and/or minor amounts of grinding are typically some of the only mechanical finishing operation(s) carried out on the more finished ceramic body. A tantalum-vapor deposition or a hydroxyapatite coating may be applied to bone-interfacing surfaces to engender ingrowth of bone. Various finished ceramic bodies to include those intended for implantation into human or animal subjects are cleaned and sterilized by known methods.

Such practice may be consolidated for illustration of preferences with reference to FIGS. 2 and 20, as follows:

Step 1: Monoclinic powder 10 is added to rubber ball cavity mold 18.

Step 2: The filled mold 18 is placed in CIP press 19.

Step 3: The press 19 is activated to provide an initial green body, for example, green block 520.

Step 4: The green block 520 is subject to bisquing if needed to provide bisqued green block 521.

Step 5: The green block 521 (or 520 if bisquing is not carried out) is machined, say, by CNC machine, to provide machined green ceramic body 530.

Step 6: The machined green ceramic body 530 is placed on suitable kiln furniture 38 in kiln 39.

Step 7: The kiln 39 is heated to fire the precursor ceramic body 530 to provide more finished ceramic body 540.

Step 8: The more finished ceramic body 540 may be processed further, for example, by polishing an articulating or bearing surface and/or by preparing for insertion such inserts as ultra high molecular weight polyethylene (UHMWPE) bushings, liners or other inserts as may be desired, and/or by sterilization, for instance, if it is for implantation as a prosthesis, to provide finally finished ceramic body 550.

Again, and with initial reference to FIG. 2 and its depicted alternate sub-procedure, the initial green body 520 of ceramic can be provided by any suitable method. Preferably, again, it is provided by using a CIP 19 on a suitable powder 10 such as a micropowder and/or nanopowder in CIP rubber mold body 18. Compare, WO 2004/080340. Thus, potential defects that may be caused by unidirectional pressing can be avoided. Again, the body 520 may be bisqued 521. Sometimes it is not. The initial green body 520, 521, 521' can be machined without embedding it in an embedding mass to make machined green body 530. A wax "handle" may be employed, in which machining wax is employed on one portion of the initial green body akin to an adhesive, without embedding it in the wax. However, even that may be avoided. For instance, the machining may be conducted with the aid of a device 600 that does not provide contact of the initial green body with an attachable substance, for example, machining wax. Thus, a mechanical grip such as a vise or chuck may be employed. As an alternative, a vacuum chuck may be employed as the device 600 to secure an initial green body 520/521 and so forth for machining. However, a green ceramic body, and especially a bisqued body may be infiltrated or impregnated with an adjuvant, for example, heated, liquid paraffin wax, which may be carried out by simple soaking in a vessel, to provide bisqued, infiltrated body 521'. The infiltration can be carried out to saturation. The body 521' can be removed from the vessel and grasped with a mechanical and/or vacuum chuck, and machined. Note, steps 4A, 4B, 4C of FIG. 2. When selecting a vacuum chuck, considerations include matching surfaces of the chuck with a suitable surface of the workpiece, and the capability to provide sufficient vacuum. Thus, a machined green ceramic body can be efficiently made. It may be clean without the necessity to remove other substances such as a wax. Should the body have been infiltrated with an adjuvant such as the paraffin wax, this is conveniently removed at oven temperatures during firing. Again, the machined green ceramic body may be fired the kiln 39 having kiln furniture 38 and/or further processed to provide more finished ceramic body 540/550. Note, FIG. 2. Thus, highly intricate detail can be provided ceramic prosthetic devices, heretofore unavailable in the art, to include not only a MgO-stabilized TTZ zirconia, posterior stabilized femoral component to a human knee, but also raised waffle pattern bumps for more secure mounting and engagement with resected bone. See, FIGS. 2-8. And so, other articles can likewise be made readily and reliably, for example, prosthetic and non-prosthetic items such as those depicted in FIGS. 9-69.

The finished ceramics can be strong, tough materials. The finished ceramic preferably embraces a surgical implant which has as a feature thereof, a smooth, articulating ceramic surface.

The finished ceramics may be light-transmissive. In turn, certain ceramic knee implant components of the invention can provide for a more rapid setting of surgical cement by use of illumination, say, with blue light, through such an implant to the cement that is in contact with both the bone stock and the implant reverse. Thus, cure and surgical times can be decreased, and a more stable bone to implant interface may be provided.

The finished ceramic knee implant parts and components can be made to be of sizes which are the same as or similar to those of corresponding parts and components made of metal. In certain cases, they may be made to be slightly larger as may be desired.

In light of the foregoing and with particular reference to FIGS. 2-8, the machined green ceramic body 530, and hence the more finished ceramic body 540 and the finally finished ceramic body 550 can be embodied as a femoral component 100 to a posterior stabilized knee. As a finally finished product, the femoral component 100, of one piece of ceramic, for the posterior stabilized knee can include frame 101 with side walls 102; top 103T; distal condylar flange 104, which may include recess 104R; posterior flange 105; and anterior flange 106. Interiorly facing bone-ingrowth enhancing and/or cement adhering surface 109 such as a porous or roughened surface can face in proximal and deep directions, and can include bumps 109B. Polymethylmethacrylate or other surgical cement can be advantageously employed. Ridges 109R may define and reinforce the frame 101 and flanges 104, 105, 106. Femoral condylar surface 110 of generally convex geometry, and advantageously of constant radius of curvature in the saggital plane, especially posteriorly, generally includes inferior, medial condyle 111; inferior, lateral condyle 112; posterior, medial condyle 113; posterior, lateral condyle 114, and may be considered to include anterior, medial condyle 115, and anterior, lateral condyle 116. On a superficial side of the anterior flange 106 can be provided trochlear surface 117, on which the natural or an artificial patella, i.e., knee cap, may generally ride. Typically the condylar and trochlear surfaces 110-117 are smooth and highly polished, for example, by use of diamond grit or dust. Intracondylar notch 118 is formed. Added stabilization is provided by posterior stop 135, which contacts a corresponding member upstanding from the tibial tray liner (not illustrated) as is well known in the art.

With particular reference to FIGS. 9-15, note the following:

FIG. 9 depicts a finally finished ceramic body 550 that is embodied as a modular femoral component 100M for a knee implant, which includes one-piece ceramic frame 101 with side walls 102; top 103T, which may have hole 103TH; distal condylar flange (not illustrated); posterior flange 105; and anterior flange 106. Femoral condylar surface 110 of generally convex geometry, again, advantageously of constant radius of curvature in the saggital plane, especially posteriorly, generally includes inferior, medial condyle 111; inferior, lateral condyle (not illustrated); posterior, medial condyle 113; posterior, lateral condyle (not illustrated); and may be considered to include anterior, medial condyle 115; and anterior, lateral condyle (not illustrated). On a superficial side of the anterior flange 106 can be provided a trochlear surface, on which the natural or an artificial knee cap may generally ride. Intracondylar notch 118 is present. Added, modular stabilization can be provided by metal or ceramic (or other suitable material) femoral bone stock insertion stem 37, which may be affixed by employment of screw 39 and/or washer 37W. Alternatively, or in addition, metal or ceramic (or other suitable material) posterior stabilization stop rod 135 may be inserted into posterior stabilization stop rod receiving hole 135H in the frame 101 so that the rod 135P traverses the notch 118. Compare, FIGS. 3-8.

FIGS. 10 and 11 depict a finally finished ceramic body 550 that is embodied as a one-piece unicompartmental knee spacer device 100U, which includes ceramic frame body 101; articular surfaces 110; anterior cusp 140A; and posterior cusp 140P. Compare, U.S. Pat. No. 6,206,927.

FIGS. 12, 13 and 14 depict a finally finished ceramic body 550 embodied as a two-piece unicompartmental joint aligning device 100UU, which includes lower ceramic frame body 101L, and upper ceramic frame body 101U; lower articular surface 110L, intermediate sliding surfaces 110S, and upper articular surface 110U; first, lower lobe 141L and first, upper lobe 141U, which may be disposed anteriorly when implanted; second, lower lobe 142L and second, upper lobe 142U, which may be disposed posteriorly when implanted; engaging post 143P; and engaging post receiving trough 143T. Compare, U.S. patent application Ser. Nos. 10/717,104 and 11/189,027.

FIG. 15 shows a ceramic temporal mandibular joint implant 100TM/550 with articular surface 110TM. The implant 100TM is in a form of a cup for mounting on a resected jaw.

FIGS. 16-19 show more or finally finished ceramic bodies 540/550 embodied as industrial components. As examples, FIG. 16 shows ceramic journal bearing 100J; FIG. 17 shows ceramic flow control apparatus 100F, including control housing 100FH, piping 100FP, and valving 100FV; control housing; FIG. 18 shows set of gears 100G; and FIG. 19 shows pulleys 100P.

FIGS. 20-49 show additional embodiments of finally finished ceramic bodies 550 for ginglymous joint implants. FIGS. 20-33 include depictions of parts or components for a rotational knee joint 1000 with natural load transfer, which includes femoral component 100 and tibial component 200; FIGS. 34, 35, 36 and 37 depict a provisional femoral component and/or a drill jig for the femoral component 100 of a knee implant such as in FIGS. 21-29 and so forth; and FIGS. 38-49 depict modular knee joint implants, which include modularity of the type that the joint or implant can be found implanted in a first configuration, and, while the joint or implant remains implanted, it can be converted to a second configuration. In consideration of these figures, the following is noted:

The femoral component 100 can include femoral component frame 101 which may be of a one-piece ceramic construction. The frame 101 can include side walls 102; front wall 103, which may have upper segment 103U, lower segment 103L, and/or hole 103H that may be tapped to receive screw 36; and top 103T, which may have hole 103TH and may have supporting flange 103F, which may accommodate inferiorly insertable intramedullary femoral spike 37, which spike 37 may be part of a boxlike module 30 that includes side walls 32, front wall 34 that may have upper portion 34U and lower portion 34L, and top 33, which mate closely with the walls 102, 103, 103U, 103L and the top 103T, and/or including hole 34H through which the screw 36 may pass on its way to the hole 103H, or which spike 37, say again, made of Cr—Co alloy, may be secured with metal washer 37W, and has screw-receiving hole 38 threaded for receiving screw 39 that also secures boxlike modular rotation device 350. The frame 101 also can include distal condylar flange 104; posterior flange 105, anterior flange 106; femoral bone stock insertion stem 107, which may be separately addable 107A to stem receptacle 107R and be secured by set screw 107S; and wall hole 108 for integral rotation device 150. Femoral bone-loss augments 104A and 105A for use together, and 104AS and 105AS for separate use, may be provided, for example, of ceramic or suitable other material such as titanium or carbon fiber, which may be coated by tantalum vapor deposition. Interiorly facing bone-ingrowth enhancing surface 109 such as a porous or roughened surface can face in proximal and deep directions, which surface 109 may also be provided a ceramic frame 101 through coating by tantalum vapor deposition techniques, as are known in the art. Femoral condylar surface 110 of generally convex geometry, and advantageously of constant radius of curvature in the saggital plane especially posteriorly, generally includes inferior, medial condyle 111; inferior, lateral condyle 112; posterior, medial condyle 113; posterior, lateral condyle 114, and may be considered to include anterior, medial condyle 115, and anterior, lateral condyle 116. As before, on a superficial side of the anterior flange 106 can be provided trochlear surface 117, on which the natural or an artificial knee cap may generally ride. Intracondylar notch 118, or inferiorly insertable module housing 301 for insertion of a modular rotation device 350 and/or the modular spike 30/37, may be formed. Again, the condylar and trochlear surfaces 110-117, as are articular surfaces in general, smooth and highly polished. Condyle-backing femoral spikes 127 may be provided. Rotation devices 150 and 350 are provided.

The rotation device 150, which may be substantially ceramic but preferably in general is metal such as Co—Cr alloy, may be embraced by UHMWPE box insert 150B, and includes rotation member 151 generally with rotation member hole 152; taper pin receptacle 153, advantageously formed with a Morse-taper-accommodating cup; and punch-pin hole 154. Axle 155, which may be secured by axle plug 155P, runs through the hole 152 and may run through radial bushing 156, say, of UHMWPE, which bushing has axle hole 157; insert shoulder 158, which fits snugly in the wall hole 108; and member-spacing shoulder 159. The rotation device 150 has highly polished taper pin 160, which can include cylindrical shaft 161; and may include extraction groove 162 to extract the pin 160 from the receptacle 153, say, with a prying tool during surgical implantation of the prosthesis 1000; extraction-restriction punch-pin locking groove 163; and taper lock tip 164, which can be made with a Morse-taper to fix the pin 160 in the cup 153. When the pin 160 is so fixed, it may be set by insertion and fit of an extraction-restriction and/or rotation-restriction punch-pin 165 through hole 154 and into groove 163. Threads 166 may be present, preferably in conjunction with Morse-taper 164, as an alternative for fastening the modular taper pin 160.

The rotation device 350 is completely modular and inferiorly insertable into the insertable modular housing 301, preferably adapted for such with its walls 102 having a Browne & Sharpe taper, say, with an about 1.5 to 2.0 degree taper 2×, or similar housing such as provided by the boxlike module with the spike 37, as an embodiment of the addable component 30, which beneficially is made of Co—Cr alloy, and can include swingable, depending male type part in housing 31 with side walls 32, preferably with a restraining Browne & Sharpe taper 32× about 1.6 to 2.1 degrees; optional top wall 33, which may have top hole 33TH; and front wall 34. Holes 52 in the side walls 52 accommodate hinge pin (axle) 55. Pivot block (rotation member) 51 can have hole 52A, which continues along the direction of the holes 52; taper pin cup 53, which may be smooth walled, tapered, say, with a Morse-taper, and/or provided with threads 56; and punch pin hole 54. The taper pin 61 is inserted in the cup 53, and may be secured through punch pin 65 and/or threads 66. The rotation device 350 may be made with a one-piece depending male type part as by having components 51 and 61 of one, integral piece.

A ceramic femoral knee component 100 may have a strength against a posterior condyle when tested in accordance with United States Food and Drug Administration (FDA) protocol of at least about 1500 pounds (lbs.); at least about 2000 lbs., or at least about 2500 lbs. Note, FIG. 4, test arrow 105T, and Example 1.

Provisional or trial femoral component 100T and/or drill jig 100DJ for the femoral component 100 may be made of ceramic according to the practice of the present invention. Sizing components 1005 ("hinge") and augment provisional or trial components 100AT may be used with the component 100T.

The tibial component 200 can include tibial component frame 201, which can have tibial tray 202; dovetail liner-insertion rails 203; liner-stopping ramp or rotation safety stop 204, and, central stop 204C, particularly if part of double-capture locking mechanism 204X; screw holes 205 through which can be inserted bone-fastening screws 206; stem 207— which may be insertable inferiorly into receiving cup 207C that may be threaded, by provision of separate stem 207Q that may be threaded also; or which may be insertable superiorly, even after implantation of the component frame 201, through hole 207H that may be threaded, by provision of the separate stem 207Q that has a superior screwing head with superior threads—and which may have distal taper 207T, a number of, say, three, distal ribbed grooves 208 and/or a number, say, two, underside flanges 208F; and interiorly facing bone-ingrowth enhancing surface 209. The tibial articular surface 210 is of concave geometry in suitable complimentarity to the convex geometry of the condylar surface 110, and generally includes superior, medial articular surface 211 and superior, lateral articular surface 212 on medial lobe 213 and lateral lobe 214, respectively. On the underside of each lobe may be dovetail grooves 215 for sliding along any rails 203; lobe-spanning portion 216; notch 217 for locking in cooperation with the stop(s) 204, 204C; and inter-condylar notch 218 analogous to the notch 118. Ramp 219 may make for an easier installment over the stop 204. Such features 200-219 may be provided on a separable tibial tray liner 220 of suitable material, for example, UHMWPE. Rotation device receptacle 250 may be in a form of an essentially cylindrical cup 251, which may have top shoulder recess 252. Rotation device receptacle liner 260, for example, UHMWPE, may be inserted into the receptacle 250 and its cup 251 so as to itself receive the taper pin 60, 160. The liner 260 can include taper pin accommodating cup 261; shoulder 262, which can fit in the recess 252; a number of, say, two to four, inside, axially directed grooves 263 to permit exit of entrained body fluids during extension and flexion of the implanted joint 1000 and consequent up and down motion of the taper pin 60, 160, which fits quite closely although movable within the liner cup 261; and outside axially directed fluid-escape feature 264, say, groove, or possible hole, to permit escape of liquids and/or gasses during insertion of the liner 260 into the receptacle 250, between which there is a close, essentially immovable-in-use fit. Shoulder bevel angles A9a and A9b may be, respectively, for example, ninety degrees and one hundred eighteen degrees.

Tibial block augments may be provided, for example, as full augment 200F or partial augment 200P. As skilled artisans would appreciate, RHK full tibial block augments 200A can only be used with RHK tibial base plates. The table, which follows, lists some augments available from Zimmer, Inc.

| Tibial Size | M/L × AP (mm) | RHK Full Augments | NexGen Partial Augments |
| --- | --- | --- | --- |
| 1 | 58 × 41 | Size 1 | Size 1 |
| 2 | 62 × 41 | Size 2 | Size 2 |
| 3 | 67 × 46 | Size 3 | Size 4 |
| 4 | 70 × 46 | Size 4 | Size 4 |
| 5 | 74 × 50 | Size 5 | Size 6 |
| 6 | 77 × 50 | Size 6 | Size 6 |

Beneficially, the knee implant 1000 has natural load transfer. As such, in addition to noted articular motions, the knee may carry a substantial amount, say, about ninety percent or more or about ninety-five percent or more of the load through the condyles.

Compare, U.S. Pat. Nos. 5,766,257 and 6,629,999.

In FIGS. 50 and 51 are depicted a zirconia ceramic, for example, Mg-TTZ ceramic, cruciate-retaining femoral component implant 100CR/550. Other ceramics such as alumina, although not as preferred, may be employed. Note, as in FIGS. 2-8, the waffle bump pattern on the bone-interfacing side of the component. This can, as with the other implants having them, provide a grip for surgical cement in addition to any rough surface on the bone-interfacing side of the component. Note, too, the ridges on the bone-interfacing side of the component, which, in addition to providing for a better cement bond, also help strengthen the implant. The implant 100CR includes smooth articular condyles 110 but has no box or other structure between the lateral and medial inferior and posterior condyles. Smooth, patella-tracking articular surface 117 is present between the condyles, especially as found between the lateral and medial anterior condyles.

In FIG. 52 is depicted a ceramic, for instance, a zirconia ceramic, say, Mg-TTZ ceramic, unicompartmental femoral knee component implant 100UK/550. Note as in FIGS. 2-8 and 38 the waffle bump pattern and ridges. The implant 100UK also includes a smooth articular condyle 110.

In FIGS. 53 and 54 are depicted a ceramic, for instance, a zirconia ceramic, again, for an example, Mg-TTZ ceramic, patellofemoral joint implant 100PF/550. It includes smooth articular surface 110 and smooth, patella-tracking articular surface 117. Note the interior ridges. A rough surface can be provided on the interior surfaces as well. Posts are provided on the bone-interfacing, interior surface in the anterior inferior position for mounting in cement on resected femoral bone stock.

FIGS. 55-58 depict ceramic, for instance, a zirconia ceramic, vertebra cap ensembles 100VC/550 for mounting between adjacent, facing vertebrae of the spine, which include smooth, spherical section articular surfaces 110. These may be implanted in the cervical, thoracic or lumbar regions, for example, in the thoracic region, say, between the ninth and tenth vertebrae essentially covering their vertebral bodies, in lieu of bone fusion when disc failure is presented. This may keep spinal flexibility an option with disc failure. In one embodiment, the vertebra cap ensemble components are mounted through a cup device in the bone-interfacing surface of the cap over resected bone. In another embodiment, the components are mounted with the assistance of posts into resected bone. Surgical cement may be employed. Of course, another material such as a suitable metal may be employed to make these vertebra cap ensembles.

FIGS. 59-64 depict ceramic, for instance, a zirconia ceramic, for example, Mg-TTZ ceramic, ankle joint ensemble having talus cap implant 100AJ and tibial tray implant 200AJ (UHMWPE tray liner not illustrated). The talus cap 100AJ has articular surface 110 to articulate with natural tissue in hemi-arthroplasty or with the tray liner in total joint replacement arthroplasty, and is in a form of a cup for mounting over a stump of resected bone as with the temporal mandibular joint 100TMJ (FIG. 15), the vertebra cap ensemble 100VC (FIGS. 55 and 56), and so forth and the like. The tibial tray implant 200AJ may be a suitable metal or even ceramic, and includes an intramedullary spike and a cup for receiving and retaining the liner having an articulating surface.

FIG. 65 depicts ceramic teeth in a ceramic body 530 in a precursor stage. These, for example, can be kiln treated to make finished ceramic bodies, say, of Mg-TTZ.

FIG. 66 depicts ice skate components 540/550, say, of Mg-TTZ.

FIGS. 67-69 depict ceramic intermediary articulation plate 202C, say, of alumina or MG-TTZ, for a tibial tray 202, say, of titanium alloy, and sliding liner 220, say of UHMWPE. Employment of the plate 202C enhances articulation of the liner 220 riding on the plate 202C, say over articulation otherwise between metal and UHMWPE. The plate 202C may be press fit and/or cemented into the tray 202, which may have circumferential lip 202L. Hole 202H may be provided through which can go a pin such as the pin 160 of a rotational knee femoral component into a rotation device receptacle 250, which may have a liner, say, of UHMWPE or even ceramic. Rotation safety stops 204, 204C, 204X may be provided to keep the liner 220 from too far a rotation as it slides on the ceramic plate 202C for which the liner is afforded accommodation as by provision of suitable "cut out" volumes to interact with the stops 204, 204C, 204X. Compare, FIGS. 28, 29, 31 and 32.

Numerous further embodiments can be effected in the practice of the invention. Thus, for example, hand and foot digit joint implants can be provided in ceramic hereby, and among these may be mentioned those of the fingers, thumb, and toes, notably, among the latter the great toe. Such an implant may have, for example, in the case of the great toe, a suitable metal tray and intramedullary spike with an attachable ceramic tray liner having an articular surface, in lieu of the all-metal construction well known in the art.

The following examples further illustrate the invention.

Example 1

A finished body of a Mg-TTZ posterior stabilized femoral knee joint implant component was begun through CIP action on an about 3-percent magnesium oxide zirconia monoclinic 1-2 um micropowder with a binder, which was bisqued to provide a right angled 3½-inch×4-inch×4-inch block. Then CNC machining of the block provided a green machined body 121.95% of the size of the projected more finished ceramic, as a precursor to a posterior stabilized femoral knee component with standard sized condyles. The precursor was placed with its condyles up on fired Mg-TTZ kiln furniture in an oven, which was ramped at an about 1~2-degree C. per minute rate from room temperature to a firing temperature of some 1725~1775 degrees C. Firing was carried out for some 2~3 hours. Then the temperature was reduced at an about 5-degree C. per minute rate to an about 1340-degree C. annealing temperature. Annealing was carried out for an about 2-hour time. The annealed ceramic was cooled to room temperature at an about 5-degree C. per minute rate to make a more finished posterior stabilized implant with great strength. See, FIGS. 2-8.

The more finished ceramic knee femoral component can have its reverse side roughened up by grinding with a diamond bit. Its articulating surfaces can be polished with diamond dust. The ceramic knee implant can be cleaned by immersion into an aqueous bath having a surfactant, with sonic agitation of the bath. Sterilization can be by radiation and/or ethylene oxide.

A fired, finished ceramic posterior stabilized knee femoral component 100 (FIGS. 2-8) made as above was designated as a demonstration model. In a demonstration, the component 100 was deliberately thrown across a room onto a hard floor to impact against a wall. The audience cringed for they had seen another ceramic knee implant shatter upon being merely dropped onto the floor, but they were awed as the demonstration component 100 remained intact.

Fired, finished ceramic posterior stabilized knee femoral components 100 (FIGS. 2-8) made as above were tested by placing them separately in a jig and then applying stress to a posterior flange 105 along the direction of test arrow 105T (FIG. 4) to correspond to the direction that the FDA would require testing of a corresponding metal component. A first ceramic component with an about 1.7-mm thickness for the walls/top 102/103 did not break when an about 1000-pound force was applied, and so the component was subjected to 15-Hz fatigue stress for 200,000 cycles with a 650-pound to 550-pound and 650-pound to 750-pound cycle without breaking. The component was broken with an about 2250-pound load, failing about its box (a wall 102 and top 103), but not the condyle flange 105. A second component with an about 1.7-mm thickness for the walls 102 was broken with an about 2300-pound load, again failing about its wall 102 and top 103 box, but not the condyle flange 105. This is generally about three times the minimum FDA value for Co—Cr.

A wall/top 102/103 of about 2~3 mm thickness is desired.

Figure 3:
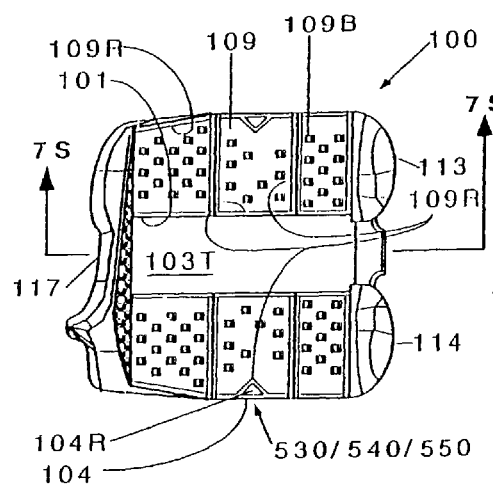
FIG. 3 shows top view of a finished ceramic body of the invention, embodied as a posterior stabilized femoral knee implant component.
Figure 4:
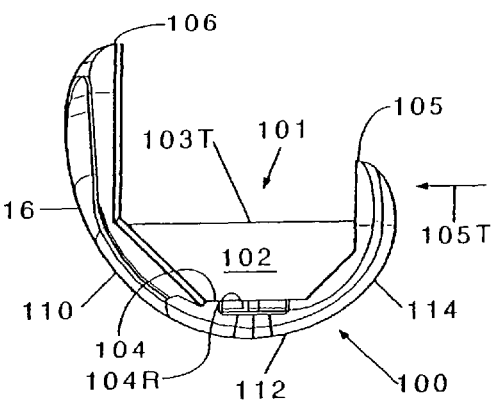
FIG. 4 shows a medial to lateral side view of the component of FIG. 3.
Figure 5:
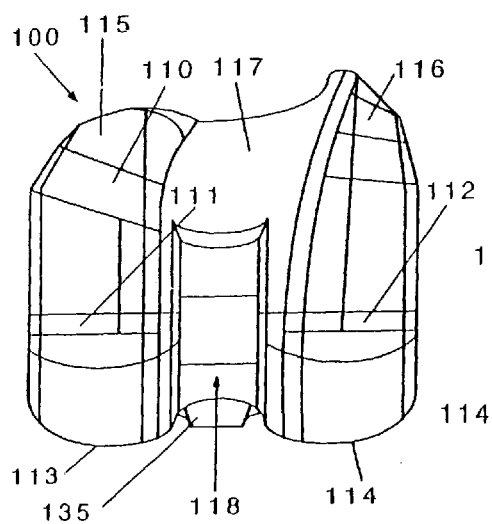
FIG. 5 shows a front view of the component of FIG. 3.
Figure 6:
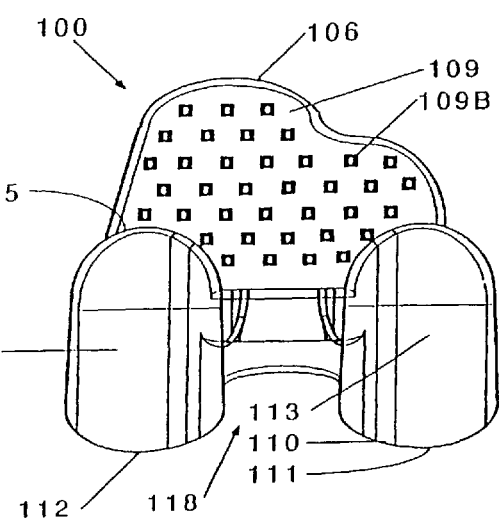
FIG. 6 shows a rear view of the component of FIG. 3.
Figure 7:
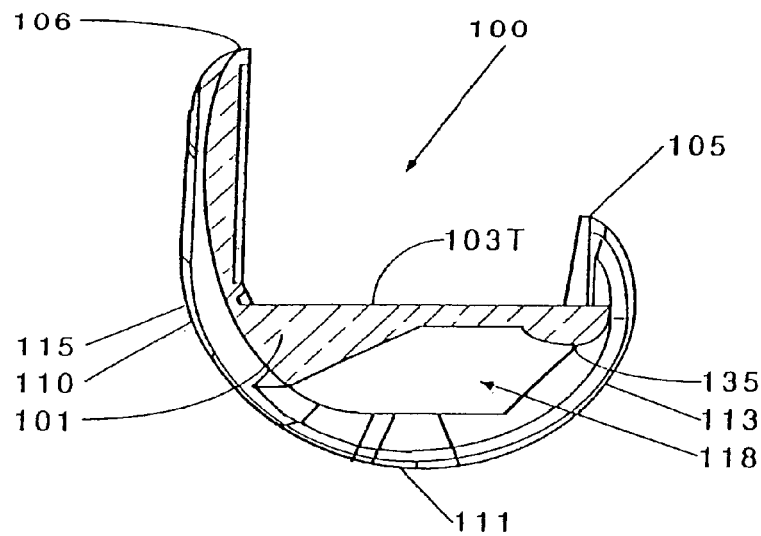
FIG. 7 is a sectional view of the component of FIG. 3, taken along 7S-7S of FIG. 3.
Figure 8:
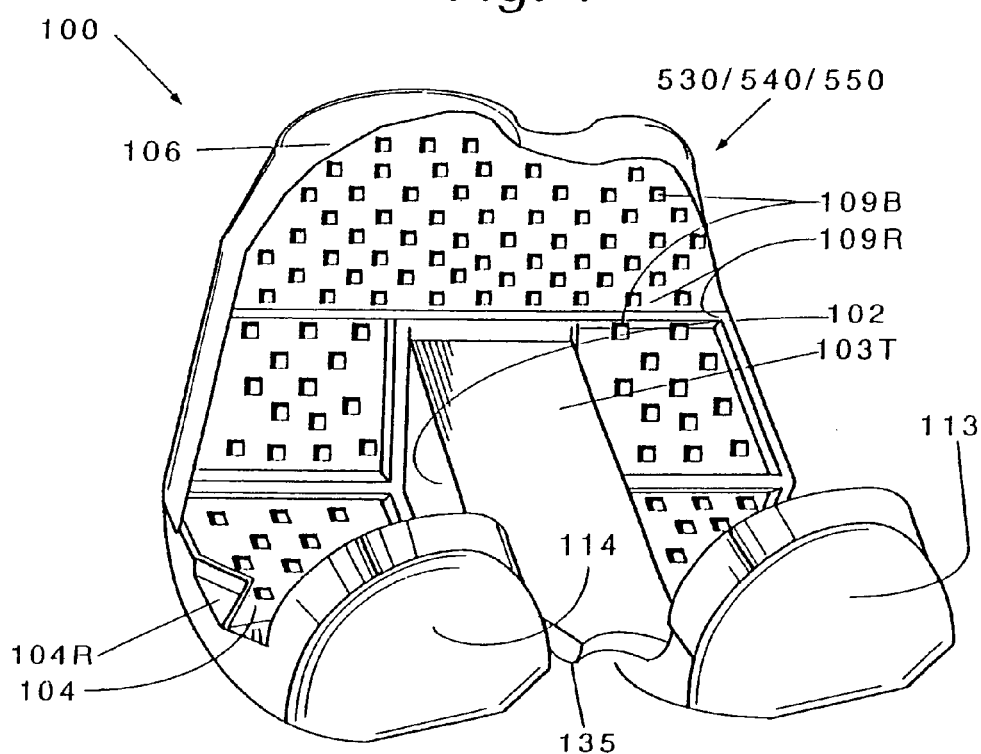
FIG. 8 is a rear, top perspective view of the component of FIG. 3.

Finite element analysis for the Mg-TTZ knee (FIGS. 2-8) with a 3-mm wall/top 102/103 thickness was carried out for stress along the arrow 105T (FIG. 4). After 88,000,000 cycles the estimated strength was a 2800-pound value.

Example 2

A block for a machined green body of for a Y-TZP posterior stabilized femoral knee joint component was made through pressure upon a monoclinic nanopowder, without binder. The block can be CNC-machined to provide a machined green ceramic body, fired and annealed, and further processed with a 1200-degree C., 20,000-psi pressure HIP to provide a theoretically dense, posterior stabilized component.

Example 3

Mg-TTZ ceramic posterior stabilized knee femoral components 100 were made by the method of Example 1 but with infiltration of a bisqued green body with paraffin wax as adjuvant, removing the infiltrated body, and then machining the removed, infiltrated, bisqued green body. See, e.g., FIGS. 2-8.

Example 4

Further ceramic products can be made by the foregoing methods. See, e.g., FIGS. 9-69.

CONCLUSION

The present invention is thus provided. Various features, parts, steps, subcombinations and combinations may be employed with or without reference to other features, parts, steps, subcombinations or combinations in its practice, and numerous adaptations and modifications can be effected within its spirit, the literal claim scope of which is particularly pointed out as follows:

What is claimed is:

1. A method for making a ceramic body prosthetic implant or prosthetic implant component of Mg-TTZ ceramic, which method comprises providing a bisqued initial green body of ceramic by providing a powdered ceramic material, which substantially is a monoclinic zirconia having magnesium oxide for a stabilizer, and, without employing a binder additional to the powdered ceramic to do so:

compressing the material in its powder form through a cold isostatic press operation to form a raw, pressed initial green body, and then heating the raw, pressed initial green body to a bisque stage to provide the bisqued initial green body; and, after the foregoing steps are carried out without the employing a binder additional to the powdered ceramic material, carrying out the following further steps:

without embedding the bisqued initial green body of ceramic in an embedding mass, machining the bisqued initial green body to provide a machined, bisqued green ceramic body such that the machined, bisqued green ceramic body has a shape, which is a precursor shape essentially analogous to, being of the same proportions as, the shape of, but larger than, the ceramic portion of a fired predetermined finished ceramic body prosthetic implant or prosthetic implant component; and then firing the machined, bisqued green ceramic body to provide a fired Mg-TTZ ceramic body product, which is the same size and shape or essentially the same size and shape as the ceramic portion of the fired predetermined finished ceramic body prosthetic implant or prosthetic implant component;

wherein a hot isostatic press operation is not carried out.

2. The method of claim 1, wherein the machined and fired ceramic body product has a density of at least about 99 percent of theoretical.

3. The method of claim 2, wherein the magnesium oxide is present at about from 3 to 3½ percent by weight.

4. The method of claim 2, wherein the heating to the bisque stage is carried out at about from 100 to 1100 degrees C.; the firing is carried out at about from 1600 to 1900 degrees C. in temperature, with ramping leading to the firing carried out at about from ½ to 20 degrees C. per minute; and anealing is carried out by gradually cooling hot, fired Mg-TTZ ceramic body, which leads to the fired Mg-TTZ ceramic body product, from the firing temperature, keeping it in a heated condition, by gradually reducing the temperature of hot, fired Mg-TTZ ceramic body below the firing temperature and keeping it there a suitable time, followed by further gradual cooling.

5. The method of claim 1, wherein the bisqued green body of ceramic is contacted by and infiltrated with an adjuvant, removed from any gross external adjuvant by which the bisqued green body of ceramic was contacted for the infiltration; and the removed, infiltrated, bisqued green body of ceramic is machined.

6. The method of claim 1, wherein the powdered ceramic material has at most an about 10-um cross-section.

7. The method of claim 1, wherein polishing is the sole mechanical finishing operation to the fired ceramic body product.

8. The method of claim 1, wherein the machined and fired ceramic body product is for or of a load-bearing intricate prosthetic implant or prosthetic implant component.

9. The method of claim 8, wherein the machined and fired ceramic body product is for or of a femoral frame component for a rotating knee joint implant.

10. The method of claim 8, wherein the machined and fired ceramic body product is for or of a femoral component for a posterior stabilized knee joint implant.

11. The method of claim 8, wherein the machined and fired ceramic body product is for or of a femoral component for a cruciate-retaining knee joint implant, which includes medial and lateral condylar articular surfaces.

12. The method of claim 8, wherein the machined and fired ceramic body product is for or of a unicompartmental femoral condylar component for a knee joint.

13. The method of claim 8, wherein the machined and fired ceramic body product is for or of an implant selected from the group consisting of a one-piece unicompartmental knee spacer device; a multi-piece unicompartmental joint aligning device; a temporal mandibular joint cap implant; a patellofemoral joint implant; a vertebra cap; an ankle joint ensemble or component; a bridge, a tooth or teeth; a tibial tray for a knee joint replacement implant; and an intermediary articulation plate for a tibial tray and liner for a knee joint replacement implant, or said plate assembed in combination with said tray.

14. The method of claim 1, wherein the machined and fired ceramic body product has a strength corresponding to that which would be provided in a femoral condylar component made of corresponding Mg-TTZ ceramic, which has a strength against a posterior condyle of said femoral condylar component of at least about 1500 pounds (about 0.68 metric tons) when tested according to United States Food and Drug Administration standards corresponding to standards for strength testing on a posterior condyle of a metal femoral knee component in which force is applied in a posterior to anterior direction on an unsupported portion of the posterior condyle.

15. The method of claim 8, wherein the machined and fired ceramic body product has a strength corresponding to that which would be provided in a femoral condylar component made of corresponding Mg-TTZ ceramic, which has a strength against a posterior condyle of said femoral condylar component of at least about 1500 pounds (about 0.68 metric tons) when tested according to United States Food and Drug Administration standards corresponding to standards for strength testing on a posterior condyle of a metal femoral knee component in which force is applied in a posterior to anterior direction on an unsupported portion of the posterior condyle.

16. The method of claim 9, wherein the machined and fired ceramic body product has a strength against a posterior condyle of said femoral frame component of at least about 1500 pounds (about 0.68 metric tons) when tested according to United States Food and Drug Administration standards corresponding to standards for strength testing on a posterior condyle of a metal femoral knee component in which force is applied in a posterior to anterior direction on an unsupported portion of the posterior condyle.

17. The method of claim 10, wherein the machined and fired ceramic body product has a strength against a posterior condyle of said femoral component of at least about 1500 pounds (about 0.68 metric tons) when tested according to United States Food and Drug Administration standards corresponding to standards for strength testing on a posterior condyle of a metal femoral knee component in which force is applied in a posterior to anterior direction on an unsupported portion of the posterior condyle.

18. The method of claim 11, wherein the machined and fired ceramic body product has a strength against a posterior condyle of said femoral component of at least about 1500 pounds (about 0.68 metric tons) when tested according to United States Food and Drug Administration standards corresponding to standards for strength testing on a posterior condyle of a metal femoral knee component in which force is applied in a posterior to anterior direction on an unsupported portion of the posterior condyle.

19. The method of claim 12, wherein the machined and fired ceramic body product has a strength against a posterior condyle of said femoral component of at least about 1500 pounds (about 0.68 metric tons) when tested according to United States Food and Drug Administration standards corresponding to standards for strength testing on a posterior condyle of a metal femoral knee component in which force is applied in a posterior to anterior direction on an unsupported portion of the posterior condyle.

20. The method of claim 13, wherein the machined and fired ceramic body product has a strength corresponding to that which would be provided in a femoral condylar component made of corresponding Mg-TTZ ceramic, which has a strength against a posterior condyle of said femoral condylar component of at least about 1500 pounds (about 0.68 metric tons) when tested according to United States Food and Drug Administration standards corresponding to standards for strength testing on a posterior condyle of a metal femoral knee component in which force is applied in a posterior to anterior direction on an unsupported portion of the posterior condyle.

21. The method of claim 1, wherein the machined and fired ceramic body product is light-transmissive so as to provide for rapid setting of surgical cement by use of illumination passed therethrough.

* * * * *